United States Patent
Furuya et al.

(10) Patent No.: US 11,877,728 B2
(45) Date of Patent: Jan. 23, 2024

(54) IMAGING MODULE AND IMAGING DEVICE

(71) Applicant: CANON KABUSHIKI KAISHA, Tokyo (JP)

(72) Inventors: Takahiro Furuya, Kanagawa (JP); Takatoshi Kamei, Kanagawa (JP); Tsutomu Inaba, Tokyo (JP); Bin Qi, Kanagawa (JP); Kei Tashiro, Kanagawa (JP); Yoshihiro Egashira, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 281 days.

(21) Appl. No.: 17/494,911

(22) Filed: Oct. 6, 2021

(65) Prior Publication Data
US 2022/0030715 A1 Jan. 27, 2022

Related U.S. Application Data

(63) Continuation of application No. PCT/JP2020/015691, filed on Apr. 7, 2020.

(30) Foreign Application Priority Data

Apr. 8, 2019 (JP) .................................. 2019-073369

(51) Int. Cl.
*A61B 1/05* (2006.01)
*H05K 1/02* (2006.01)
(Continued)

(52) U.S. Cl.
CPC ............. *A61B 1/051* (2013.01); *H04N 23/50* (2023.01); *H05K 1/028* (2013.01); *H05K 1/118* (2013.01);
(Continued)

(58) Field of Classification Search
CPC ............ A61B 1/00018; A61B 1/00105; A61B 1/0011; A61B 1/051; G02B 23/24;
(Continued)

(56) References Cited

U.S. PATENT DOCUMENTS 6,671,347 B2   12/2003   Tashiro et al.
6,801,598 B2   10/2004   Tashiro et al.
(Continued)

FOREIGN PATENT DOCUMENTS

JP   2001-027734 A   1/2001
JP   3158863 U   4/2010
(Continued)

OTHER PUBLICATIONS

International Search Report and Written Opinion for International Patent Application No. PCT/JP2020/015691.

*Primary Examiner* — Amy R Hsu
(74) *Attorney, Agent, or Firm* — Venable LLP

(57) ABSTRACT

An imaging module includes an electric cable including a plurality of wirings, an imager having an imaging surface intersecting an axial direction of a distal end of the electric cable, and a flexible wiring board configured to electrically connect the imager and the electric cable. The wiring board includes a plurality of extending portions that extend from at least three portions of a connection portion connected with the imager. At least one wiring pad to which at least one of the plurality of wirings of the electric cable is connected is provided in each of the plurality of extending portions.

13 Claims, 14 Drawing Sheets

(51) Int. Cl.
*H05K 1/11* (2006.01)
*H04N 23/50* (2023.01)
*A61B 1/00* (2006.01)

(52) U.S. Cl.
CPC ........ *A61B 1/00105* (2013.01); *H04N 23/555* (2023.01); *H05K 2201/09027* (2013.01); *H05K 2201/0939* (2013.01); *H05K 2201/09445* (2013.01)

(58) Field of Classification Search
CPC ...... H04N 23/50; H04N 23/555; H05K 1/028; H05K 1/118; H05K 1/189; H05K 2201/052; H05K 2201/09027; H05K 2201/0939; H05K 2201/09445; H05K 2201/10356
See application file for complete search history.

(56) References Cited

U.S. PATENT DOCUMENTS

| | | | |
|---|---|---|---|
| 6,847,698 | B2 | 1/2005 | Kaifu et al. |
| 6,947,084 | B2 | 9/2005 | Kaifu et al. |
| 7,050,538 | B2 | 5/2006 | Tashiro et al. |
| 7,589,774 | B2 | 9/2009 | Kaifu et al. |
| 2015/0228678 | A1* | 8/2015 | Yoshida ................. H04N 23/54 600/110 |
| 2016/0029879 | A1* | 2/2016 | Ishikawa ................ A61B 1/005 600/110 |
| 2019/0298153 | A1* | 10/2019 | Sato ................... A61B 1/00018 |
| 2021/0007584 | A1* | 1/2021 | Heni ................... A61B 1/0661 |

FOREIGN PATENT DOCUMENTS

| | | |
|---|---|---|
| JP | 2011-217887 A | 11/2011 |
| JP | 2014-087705 A | 5/2014 |

* cited by examiner

F I G. 14
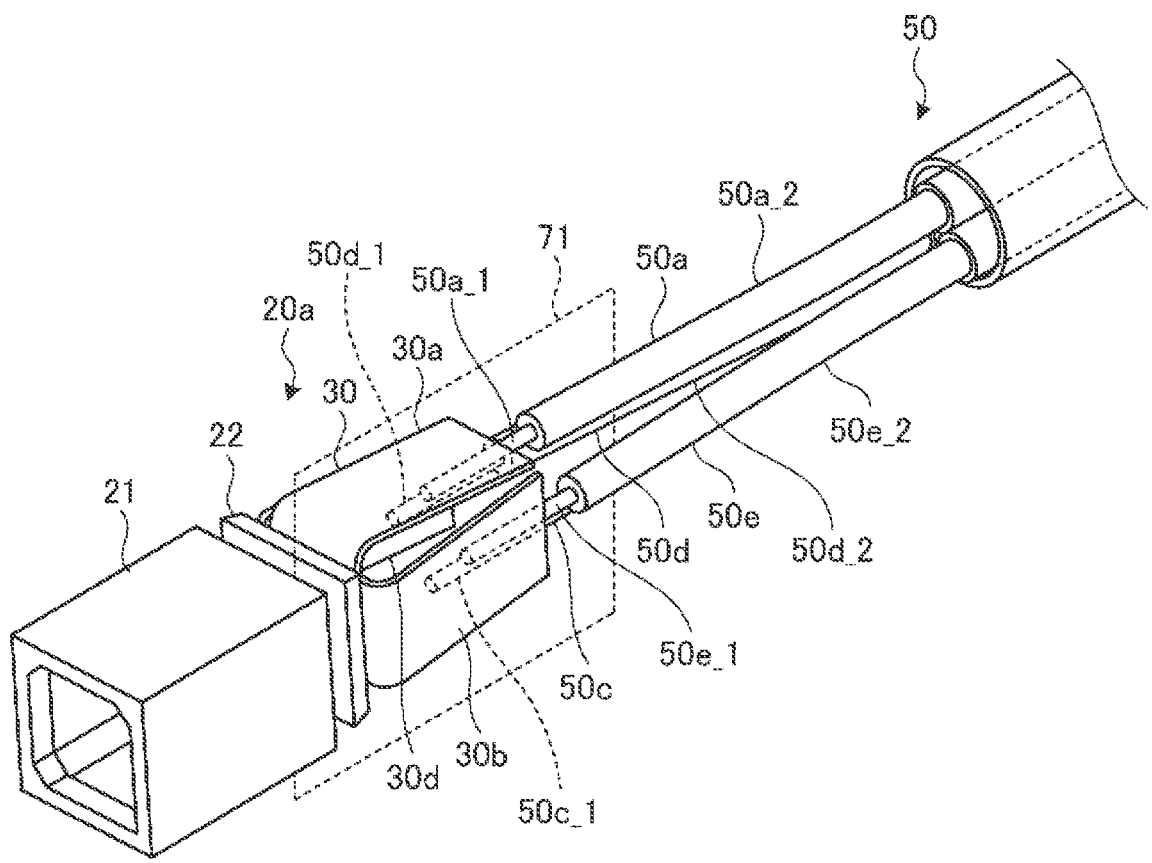

IMAGING MODULE AND IMAGING DEVICE

CROSS-REFERENCE TO RELATED APPLICATIONS

This application is a Continuation of International Patent Application No. PCT/JP2020/015691, filed Apr. 7, 2020, which claims the benefit of Japanese Patent Application No. 2019-073369, filed Apr. 8, 2019, both of which are hereby incorporated by reference herein in their entirety.

BACKGROUND OF THE INVENTION

Field of the Invention

Embodiments of the present invention relate to an imaging module and an imaging device.

BACKGROUND ART

Conventionally, there is provided an ultra-small imaging device used as an endoscopic device. For example, there is provided a head separated imaging device in which a camera head with an image sensor and a camera control unit for processing an image signal transmitted from the camera head are separated from each other. The image sensor is, for example, a CCD (Charge Coupled Device) image sensor or a CMOS (Complementary Metal Oxide Semiconductor) image sensor. In the head separated imaging device, the camera head and the camera control unit are connected by an electric cable. The electric cable stores a plurality of wirings.

A case in which the image sensor and the wirings are directly connected will now be described. In this case, it is necessary to adjust the positions of connection portions (portions connected to the image sensor) of the connected wirings to be aligned with the image sensor. However, for example, in the ultra-small endoscopic device, the diameter of a cylindrical scope inserted into a subject is about 1 mm. Furthermore, for example, the length of one side of a rectangular image sensor is equal to or less than 1 mm. In such ultra-small imaging device used as an ultra-small endoscopic device, it is possible to change the direction and shape of each of the plurality of wirings only within the range of the scope having a diameter of about 1 mm.

Therefore, it is extremely difficult to directly connect the image sensor and the wirings. To cope with this, in such ultra-small imaging device, a relay member for connecting the image sensor and the plurality of wirings in the electric cable is used. The use of such relay member makes it possible to readily align the pads of the image sensor and the wirings. As the relay member, for example, an FPC (Flexible Printed Circuits) is used. The image sensor and the plurality of wirings in the electric cable are electrically connected to wirings formed in the FPC. For example, a plurality of pads formed in the FPC are connected to the plurality of wirings, respectively, in the electric cable by soldering. However, even if the FPC is used, the areas of the pads for electrically connecting the plurality of wirings are very small, and a phenomenon that two adjacent pads are electrically connected via a solder portion, that is, a so-called bridge or the like may occur at the time of soldering.

CITATION LIST

Patent Literature

PTL 1: Japanese Patent Laid-Open No. 2011-217887

SUMMARY OF INVENTION

One embodiment provides an imaging module and an imaging device that can readily perform wiring connection while suppressing occurrence of a bridge or the like.

An imaging module according to the embodiment comprises an electric cable, an imager, and a wiring board. The electric cable includes a plurality of wirings. The imager has an imaging surface intersecting an axial direction of a distal end of the electric cable. The wiring board electrically connects the imager and the electric cable. The wiring board is flexible. The wiring board includes a plurality of extending portions that extend from at least three portions of a connection portion connected with the imager. At least one wiring pad to which at least one of the plurality of wirings of the electric cable is connected is provided in each of the plurality of extending portions.

Other features and advantages of the present invention will be apparent from the following description taken in conjunction with the accompanying drawings. Note that the same reference numerals denote the same or like components throughout the accompanying drawings.

BRIEF DESCRIPTION OF DRAWINGS

The accompanying drawings, which are incorporated in and constitute a part of the specification, illustrate embodiments of the invention and, together with the description, serve to explain principles of the invention.

FIG. 14 is a view showing an example of the arrangement of a camera head and an electric cable according to the second embodiment;

DESCRIPTION OF THE EMBODIMENTS

Figure 1:
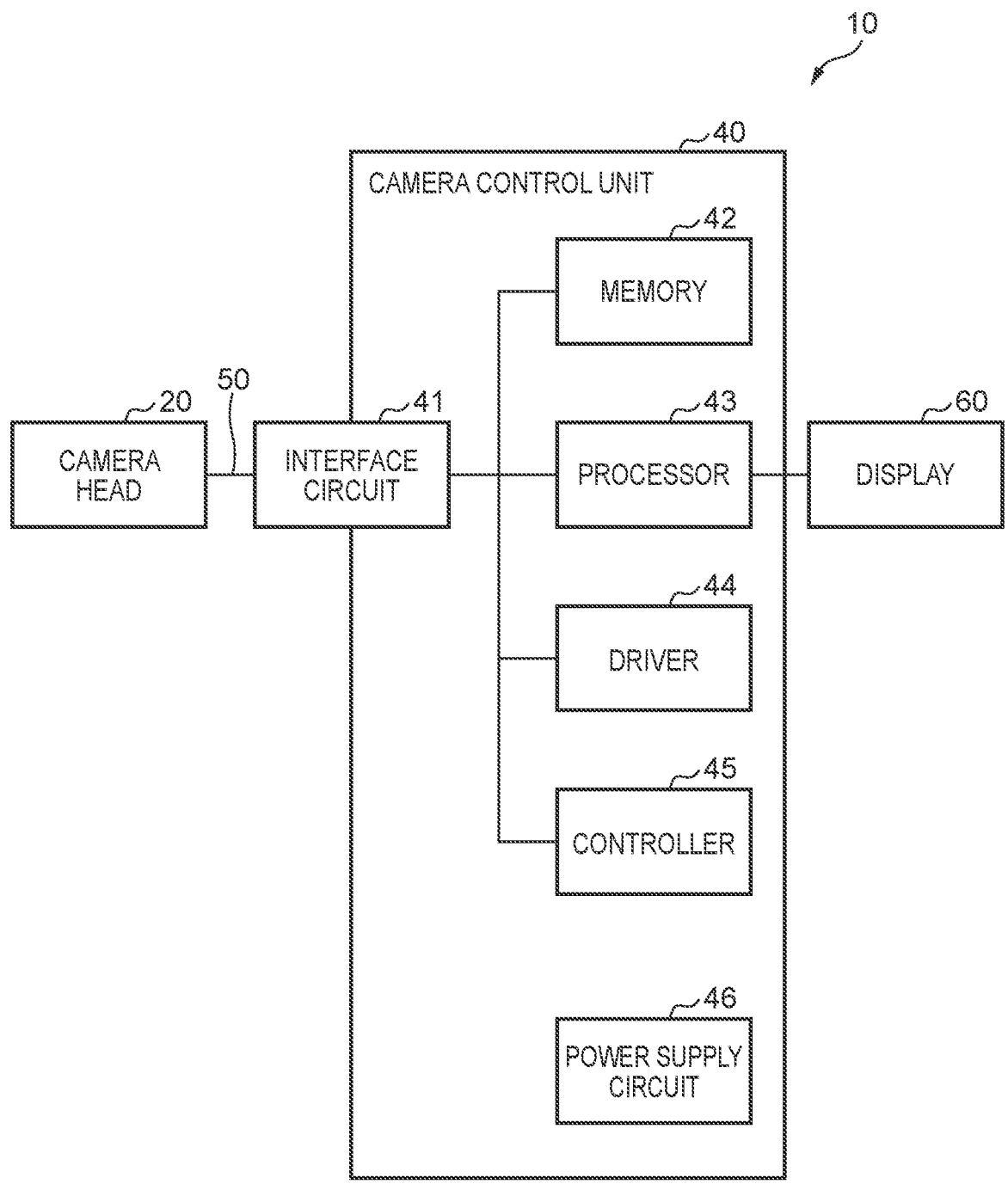
FIG. 1 is a block diagram showing an example of the arrangement of an imaging device according to the first embodiment.

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

Embodiments of an imaging module and an imaging device will be described in detail below with reference to the accompanying drawings. Note that an imaging module and an imaging device according to the present invention are not limited by the following embodiments.

First Embodiment

FIG. 1 is a block diagram showing an example of the arrangement of an imaging device 10 according to the first embodiment. The imaging device 10 is, for example, a device that is used as a medical endoscope to image the inside of a subject. For example, the imaging device 10 is used as an ultra-small endoscope. As shown in FIG. 1, the imaging device 10 includes a camera head 20, a CCU (Camera Control Unit) 40, and an electric cable 50. The imaging device 10 is a head separated imaging device in which the camera head 20 and the camera control unit 40 are separated from each other.

The camera head 20 images the inside of a subject, and transmits an image signal obtained by imaging to the camera control unit 40 via the electric cable 50. If the imaging device 10 is used as a medical endoscope, the camera head 20 is provided in a cylindrical scope (not shown) inserted into the subject. For example, the diameter of the scope is amount 1 mm. The camera head 20 is an example of an imaging module. Details of the camera head 20 will be described later.

The camera control unit 40 processes the image signal transmitted from the camera head 20. The camera control unit 40 includes an interface (IF) circuit 41, a memory 42, a processor 43, a driver 44, a controller 45, and a power supply circuit 46.

The interface circuit 41 is an interface for transmitting/receiving various signals and data to/from the camera head 20 via the electric cable 50.

The memory 42 is, for example, a nonvolatile memory. The memory 42 is, for example, a serial EEPROM (Electrically Erasable Programmable Read-Only Memory). The memory 42 stores setting data and correction data of the camera head 20.

The processor 43 is an image processing processor. The processor 43 performs various image processes (for example, image processes such as noise correction, white balance, and y correction) such as correction processing for the image signal transmitted from the camera head 20 under the control of the controller 45. Then, the processor 43 outputs the image signal having undergone the various image processes to an external display 60. This causes the display 60 to display an image based on the image signal output from the processor 43. The display 60 is, for example, a liquid crystal display or a CRT (Cathode Ray Tube).

The driver 44 is a driving circuit for driving the image sensor 22 (to be described later) of the camera head 20. The driver 44 changes the driving method and frame rate of the image sensor 22 under the control of the controller 45. The driver 44 transmits a synchronization signal (for example, a pulse signal for vertical synchronization or horizontal synchronization) to the image sensor 22. The driver 44 transmits the above-described synchronization signal to the image sensor 22 via the interface circuit 41 and the electric cable 50.

The controller 45 reads out the correction data and the setting data from the memory 42. Then, the controller 45 controls the processor 43 and the driver 44 based on the readout correction data and setting data.

The power supply circuit 46 is connected to an external power supply. The power supply circuit 46 converts power from the external power supply into a predetermined voltage. Then, the power supply circuit 46 supplies power based on the predetermined voltage to a plurality of circuits (the interface circuit 41, the memory 42, the processor 43, the driver 44, and the controller 45) forming the camera control unit 40. The power supply circuit 46 also supplies power to the image sensor 22 (to be described later) via the electric cable 50.

Figure 2:
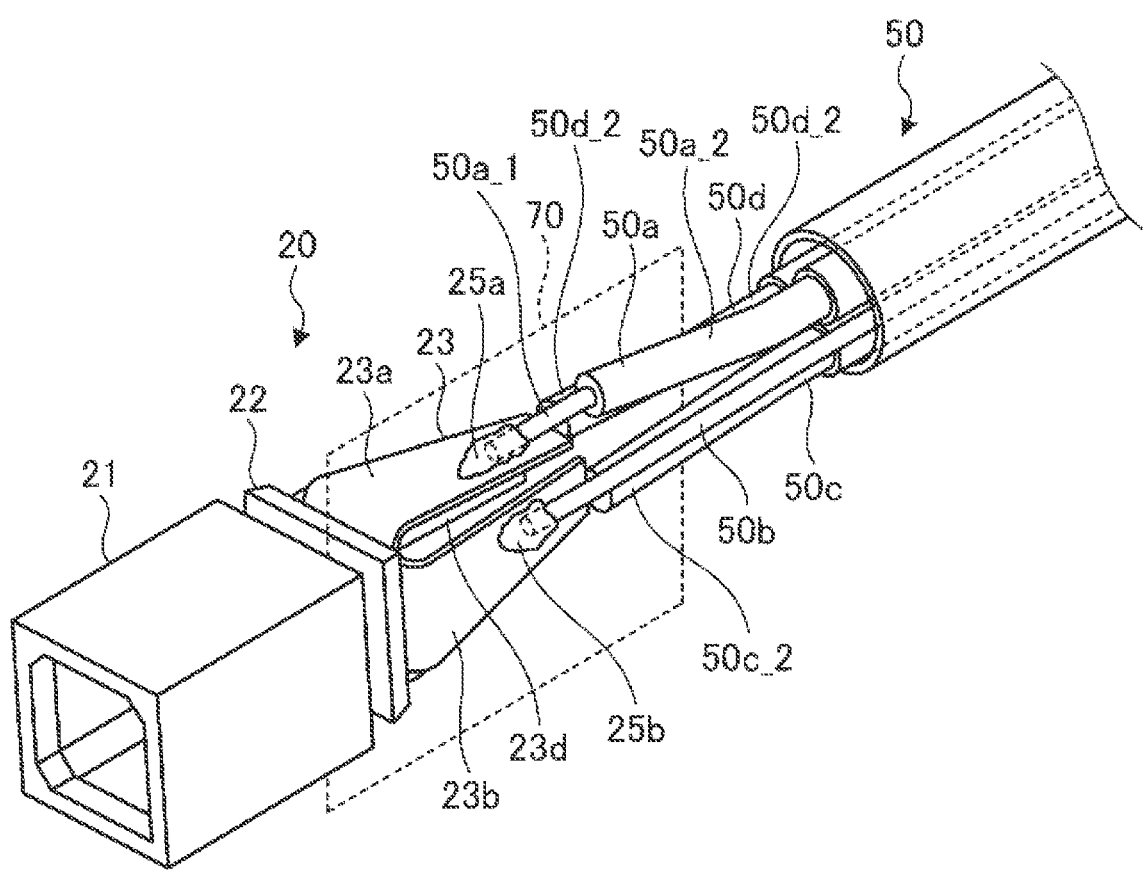
FIG. 2 is a view showing an example of the arrangement of a camera head and an electric cable according to the first embodiment.

FIG. 2 is a view showing an example of the arrangement of the camera head 20 and the electric cable 50 according to the first embodiment. As shown in FIG. 2, the camera head 20 includes a lens housing 21, an image sensor 22, a flexible printed circuit 23, and a plurality of solder portions 25a and 25b. Although not shown in FIG. 2, the camera head 20 includes a solder portion 25c (see FIG. 7) for electrically connecting a wiring 50c of the electric cable 50 and the flexible printed circuit 23. The camera head 20 also includes a solder portion (not shown) for electrically connecting a wiring 50d of the electric cable 50 and the flexible printed circuit 23.

The lens housing 21 includes a lens (not shown). This lens forms an image of light having entered the lens on the imaging surface of the image sensor 22.

The image sensor 22 is, for example, a CCD image sensor or a CMOS image sensor. The image sensor 22 includes the imaging surface on which a plurality of imaging elements (pixels) are arranged in a matrix. Each of the plurality of imaging elements generates an image signal (electrical signal) by receiving light, and outputs the generated image signal to the camera control unit 40 via the electric cable 50. The image sensor 22 is an example of an imager.

Figure 3:
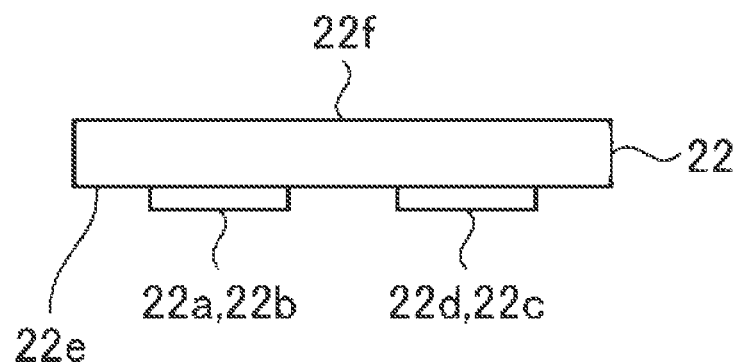
FIG. 3 is a side view of an image sensor according to the first embodiment.
Figure 4:
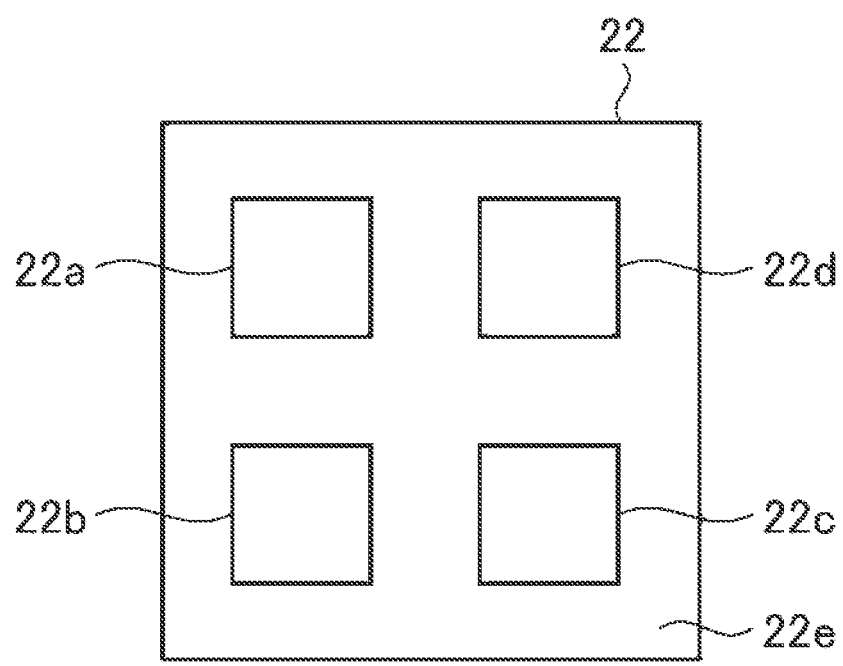
FIG. 4 is a rear view showing the lower surface of the image sensor according to the first embodiment.

FIG. 3 is a side view of the image sensor 22 according to the first embodiment. FIG. 4 is a rear view showing a lower surface 22e of the image sensor 22 according to the first embodiment. Note that a surface, on the light incident side, of the image sensor 22 is set as an upper surface 22f and a surface on the opposite side of the upper surface 22f is set as the lower surface 22e.

As exemplified in FIGS. 3 and 4, the image sensor 22 is a rectangular member. For example, the image sensor 22 is a square member in a front view. The image sensor 22 includes the upper surface 22f and the lower surface 22e.

A plurality of imaging elements are arranged in a matrix on the upper surface 22f of the image sensor 22. That is, the imaging surface exists on the side of the upper surface 22f. The image sensor 22 is arranged so that this imaging surface faces the lens in the above-described lens housing 21. Note that a cover glass for protecting the imaging surface may be provided on the upper surface 22f.

A plurality (four) of pads 22a to 22d are provided on the lower surface 22e of the image sensor 22. For example, the image sensor 22 outputs the image signal via the pad 22a. Furthermore, the image sensor 22 performs various operations based on a reference voltage indicating a reference potential applied to the pad 22b and a synchronization signal input to the pad 22c. For example, the image sensor 22 can operate when power is supplied via the pad 22d.

Figure 5:
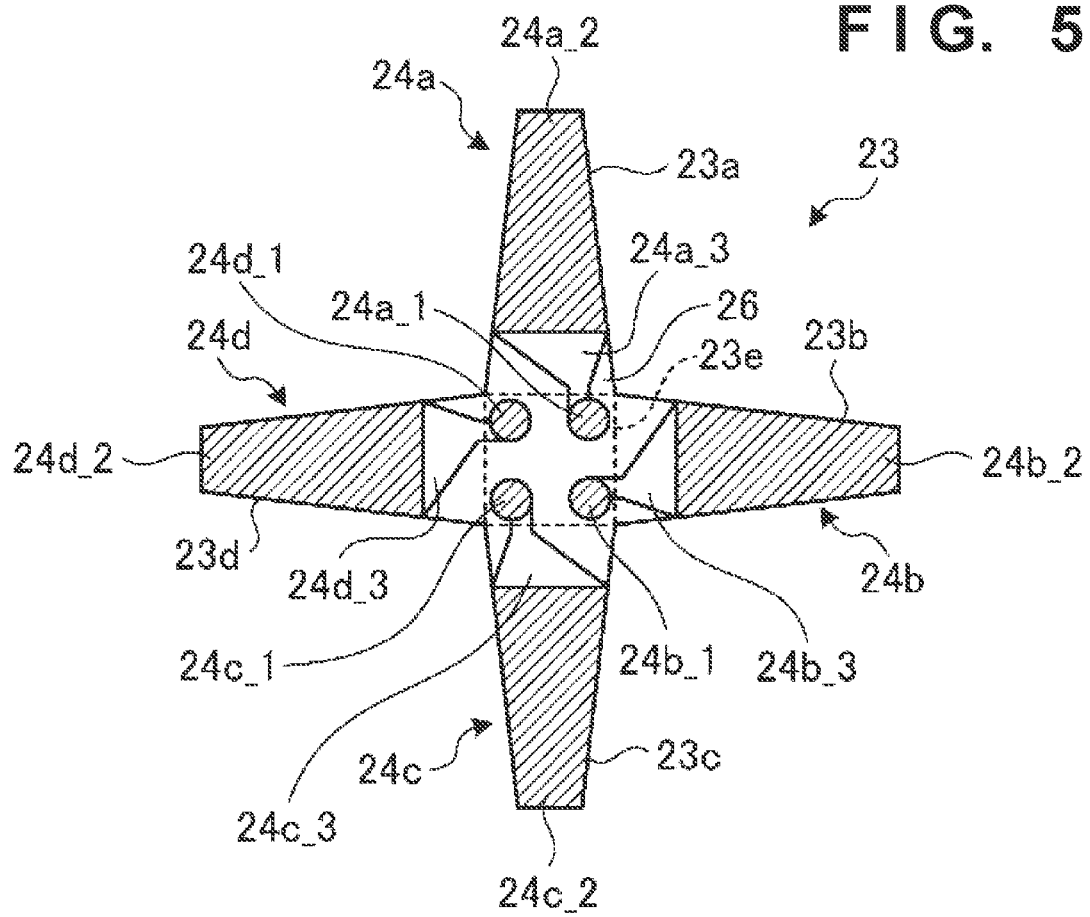
FIG. 5 is a view showing an example of a flexible printed circuit according to the first embodiment.

FIG. 5 is a view showing an example of the flexible printed circuit 23 according to the first embodiment. FIG. 5 is a front view showing an upper surface 26 of the flexible printed circuit 23. Note that in this embodiment, a side of the flexible printed circuit 23 connected to the image sensor 22 is set as an upper side and a surface on the side connected to the image sensor 22 is set as the upper surface 26. The surface on the opposite side of the upper surface 26 of the flexible printed circuit 23 is set as a lower surface 27 (see FIG. 6). The flexible printed circuit 23 is an example of a flexible wiring board. The flexible printed circuit 23 electrically connects the image sensor 22 and the electric cable 50. Note that if the flexible printed circuit 23 is used as a part forming the imaging device 10, the flexible printed circuit 23 is used in a bent state, as shown in FIG. 2. However, FIG. 5 shows an example of the flexible printed circuit 23 in a non-bent state.

The flexible printed circuit 23 is, for example, a single-sided flexible printed circuit (single-sided FPC). As exemplified in FIG. 5, the flexible printed circuit 23 includes a plurality (four) of extending portions 23a to 23d and a connection portion 23e. The surface on the upper side of the connection portion 23e is a region (implementation region) where the image sensor 22 is implemented, and is a region (connection region) connected to the image sensor 22. As exemplified in FIG. 5, the four extending portions 23a to 23d extend from the connection portion 23e in four directions. More specifically, the four extending portions 23a to 23d extend in directions different from each other by 90°. The four extending portions 23a to 23d extend from four portions of the connection portion 23e connected to the image sensor 22.

As exemplified in FIG. 5, each of the four extending portions 23a to 23d has a width that gradually decreases as the distance from the connection portion 23e increases. That is, each of the four extending portions 23a to 23d has a so-called tapered shape.

In the imaging device 10, the flexible printed circuit 23 is bent at the boundary between each of the four extending portions 23a to 23d and the connection portion 23e.

On the upper surface 26 of the flexible printed circuit 23, four wirings 24a to 24d are formed. The wiring portion 24a includes a pad 24a_1, a pad 24a_2, and a wire connection portion 24a_3.

The pad 24a_1 is formed in the connection portion 23e. The pad 24a_1 is formed at a position corresponding to the pad 22a of the image sensor 22. For example, the pad 24a_1 is formed at a position facing the pad 22a. The pad 24a_1 is electrically connected to the pad 22a. For example, the pad 24a_1 is connected to the pad 22a via a solder portion (not shown) by soldering.

The pad 24a_2 is formed in the extending portion 23a. The pad 24a_2 is electrically connected to a wiring 50a (to be described later) of the electric cable 50. For example, the pad 24a_2 is connected to the wiring portion 50a via the solder portion 25a by soldering. The pad 24a_2 is an example of a wiring pad.

The wire connection portion 24a_3 is formed across the connection portion 23e and the extending portion 23a. The wire connection portion 24a_3 electrically connects the pads 24a_1 and 24a_2. Therefore, the wiring portion 50a (to be described later) and the image sensor 22 are electrically connected to each other.

The wiring portion 24b includes a pad 24b_1, a pad 24b_2, and a wire connection portion 24b_3.

The pad 24b_1 is formed in the connection portion 23e. The pad 24b_1 is formed at a position corresponding to the pad 22b of the image sensor 22. For example, the pad 24b_1 is formed at a position facing the pad 22b. The pad 24b_1 is electrically connected to the pad 22b. For example, the pad 24b_1 is connected to the pad 22b via a solder portion (not shown) by soldering.

The pad 24b_2 is formed in the extending portion 23b. The pad 24b_2 is electrically connected to a wiring 50b (to be described later) of the electric cable 50. For example, the pad 24b_2 is connected to the wiring portion 50b via the solder portion 25b by soldering. The pad 24b_2 is an example of a wiring pad.

The wire connection portion 24b_3 is formed across the connection portion 23e and the extending portion 23b. The wire connection portion 24b_3 electrically connects the pads 24b_1 and 24b_2. Therefore, the wiring portion 50b (to be described later) and the image sensor 22 are electrically connected to each other.

The wiring portion 24c includes a pad 24c_1, a pad 24c_2, and a wire connection portion 24c_3.

The pad 24c_1 is formed in the connection portion 23e. The pad 24c_1 is formed at a position corresponding to the pad 22c of the image sensor 22. For example, the pad 24c_1 is formed at a position facing the pad 22c. The pad 24c_1 is electrically connected to the pad 22c. For example, the pad 24c_1 is connected to the pad 22c via a solder portion (not shown) by soldering.

The pad 24c_2 is formed in the extending portion 23c. The pad 24c_2 is electrically connected to the wiring portion 50c (to be described later) of the electric cable 50. For example, the pad 24c_2 is connected to the wiring portion 50c via the solder portion 25c (see FIG. 7) by soldering. The pad 24c_2 is an example of a wiring pad.

The wire connection portion 24c_3 is formed across the connection portion 23e and the extending portion 23c. The wire connection portion 24c_3 electrically connects the pads 24c_1 and 24c_2. Therefore, the wiring portion 50c (to be described later) and the image sensor 22 are electrically connected to each other.

The wiring portion 24d includes a pad 24d_1, a pad 24d_2, and a wire connection portion 24d_3.

The pad 24d_1 is formed in the connection portion 23e. The pad 24d_1 is formed at a position corresponding to the pad 22d of the image sensor 22. For example, the pad 24d_1 is formed at a position facing the pad 22d. The pad 24d_1 is electrically connected to the pad 22*d*. For example, the pad 24*d*_1 is connected to the pad 22*d* via a solder portion (not shown) by soldering.

The pad 24*d*_2 is formed in the extending portion 23*d*. The pad 24*d*_2 is electrically connected to the wiring portion 50*d* (to be described later) of the electric cable 50. For example, the pad 24*d*_2 is connected to the wiring portion 50*d* via a solder portion (not shown) by soldering. The pad 24*d*_2 is an example of a wiring pad.

The wire connection portion 24*d*_3 is formed across the connection portion 23*e* and the extending portion 23*c*. The wire connection portion 24*d*_3 electrically connects the pads 24*d*_1 and 24*d*_2. Therefore, the wiring portion 50*d* (to be described later) and the image sensor 22 are electrically connected to each other.

Figure 6:
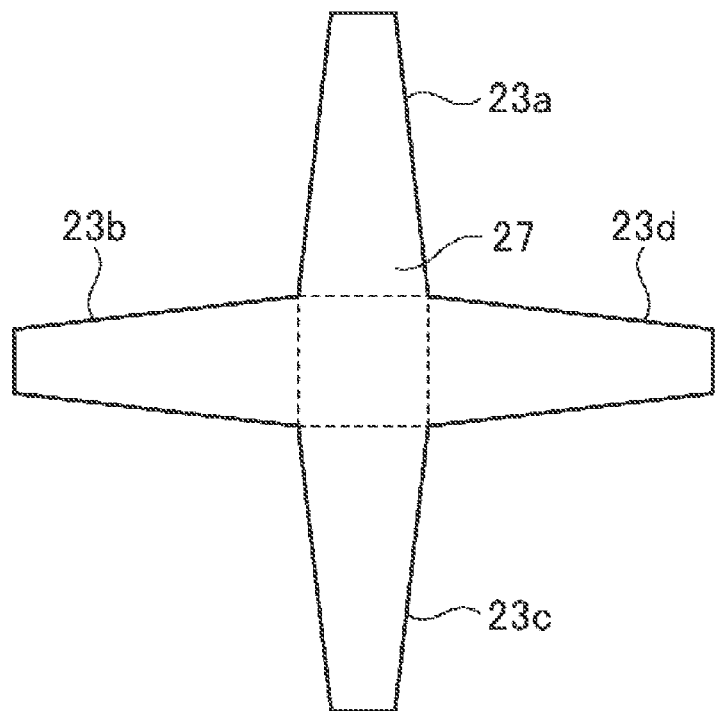
FIG. 6 is a rear view showing the lower surface of the flexible printed circuit according to the first embodiment.

FIG. 6 is a rear view showing the lower surface 27 of the flexible printed circuit 23 according to the first embodiment. As exemplified in FIG. 6, no wirings are formed on the side of the lower surface 27 of the flexible printed circuit 23. Broken lines shown in FIG. 6 indicate portions where the flexible printed circuit 23 is bent.

Referring back to FIG. 2, the electric cable 50 includes a plurality of wirings the number of which is equal to the number of the plurality of pads 22*a* to 22*d* of the image sensor 22. More specifically, the electric cable 50 includes the four wirings 50*a* to 50*d*. Note that the electric cable 50 may include a plurality of wirings the number of which is different from four. A case in which the electric cable 50 includes the four wirings 50*a* to 50*d* will be described below. Each of the four wirings 50*a* to 50*d* is connected to the flexible printed circuit 23 so that the axial direction of the distal end, on the side of the flexible printed circuit 23, of each of the four wirings 50*a* to 50*d* intersects the imaging surface of the image sensor 22. That is, the imaging surface of the image sensor 22 intersects the axial direction of the distal end of the electric cable 50.

The wiring portion 50*a* is a wiring through which the image signal is transmitted. The wiring portion 50*a* includes a core 50*a*_1 and a covering material 50*a*_2. The core 50*a*_1 is a conductor through which the image signal flows. The covering material 50*a*_2 is made of an insulating material such as vinyl. The covering material 50*a*_2 covers the core 50*a*_1. However, as shown in FIG. 2, the distal end portion of the core 50*a*_1 is not covered with the covering material 50*a*_2 and is exposed so as to be connectable to the extending portion 23*a* of the flexible printed circuit 23. The core 50*a*_1 is connected to the pad 24*a*_2 via the solder portion 25*a* by soldering.

The wiring portion 50*b* is a wiring used as ground (GND). In the example shown in FIG. 2, the wiring portion 50*b* is a core. The wiring portion 50*b* is connected to the pad 24*b*_2 via the solder portion 25*b* by soldering. This applies a reference voltage indicating a reference potential to the pad 22*b* of the image sensor 22 via the pad 24*b*_2.

The wiring portion 50*c* is a wiring through which the synchronization signal is transmitted. Similar to the wiring portion 50*a*, the wiring portion 50*c* includes a core 50*c*_1 (see FIG. 7) and a covering material 50*c*_2. The core 50*c*_1 is a conductor through which the synchronization signal flows. The covering material 50*c*_2 is made of an insulating material such as vinyl. The covering material 50*c*_2 covers the core 50*c*_1. However, the distal end portion of the core 50*c*_1 is not covered with the covering material 50*c*_2 and is exposed so as to be connectable to the extending portion 23*c* of the flexible printed circuit 23. The core 50*c*_1 is connected to the pad 24*c*_2 via the solder portion 25*c* (see FIG. 7) by soldering.

The wiring portion 50*d* is a power supply wiring portion. Similar to the wirings 50*a* and 50*c*, the wiring portion 50*d* includes a core (not shown) and a covering material 50*d*_2. The core of the wiring portion 50*d* is a conductor for supplying power. The covering material 50*d*_2 is made of an insulating material such as vinyl. The covering material 50*d*_2 covers the core of the wiring portion 50*d*. However, the distal end portion of the core is not covered with the covering material 50*d*_2 and is exposed so as to be connectable to the extending portion 23*d* of the flexible printed circuit 23. The core of the wiring portion 50*d* is connected to the pad 24*d*_2 via a solder portion (not shown) by soldering.

As described above, according to this embodiment, only one pad (24*a*_2, 24*b*_2, 24*c*_2, 24*d*_2) is provided in one extending portion (23*a*, 23*b*, 23*c*, 23*d*). Therefore, it is possible to ensure a wide area for one pad. Thus, according to this embodiment, a developer who performs soldering or the like can readily perform wiring connection to the pad. Furthermore, in one extending portion, only one pad is provided without arranging a plurality of pads to be adjacent to each other. Therefore, according to this embodiment, it is possible to suppress occurrence of a bridge or the like. That is, according to this embodiment, it is possible to readily perform wiring connection while suppressing occurrence of a bridge or the like.

Next, an example of the positional relationship among the image sensor 22, each of the plurality of wirings 50*a* and 50*c*, and each of the plurality of solder portions 25*a* and 25*c* for respectively connecting the plurality of wirings 50*a* and 50*c* to the flexible printed circuit 23 will be described with reference to FIG. 7.

Figure 7:
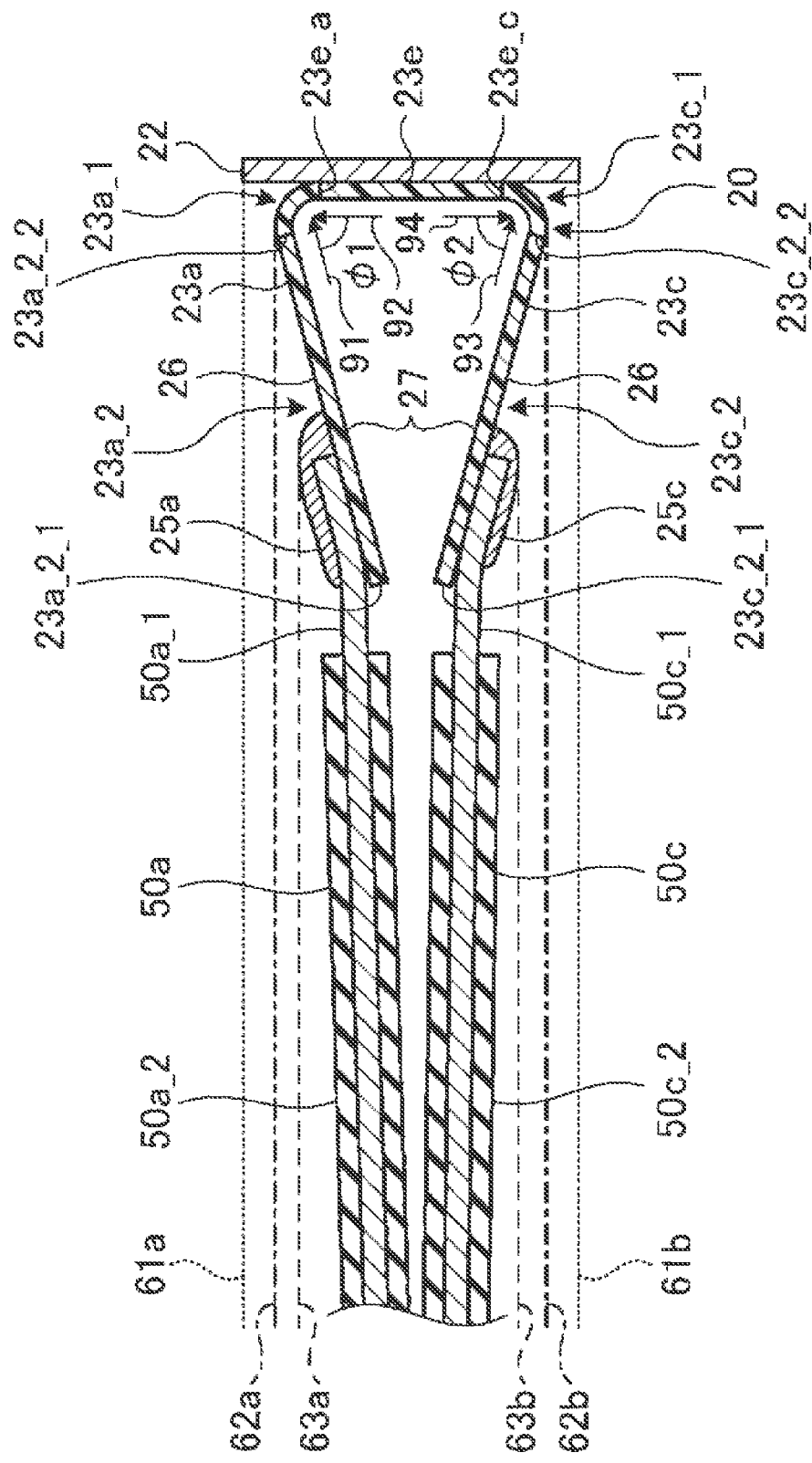
FIG. 7 is a view for explaining an example of the positional relationship among the image sensor, each of a plurality of wirings, and each of a plurality of solder portions.

FIG. 7 is a view for explaining an example of the positional relationship among the image sensor 22, each of the plurality of wirings 50*a* and 50*c*, and each of the plurality of solder portions 25*a* and 25*c*. FIG. 7 is a sectional view showing a section 70 that is indicated by a broken line in FIG. 2, is orthogonal to the imaging surface of the image sensor 22, and passes through the wirings 50*a* and 50*c*.

FIG. 7 shows, in a sectional view, line segments 61*a* and 61*b* representing the position of the outer shape of the image sensor 22, line segments 62*a* and 62*b* representing the position of the outer shape of the flexible printed circuit 23, and line segments 63*a* and 63*b* respectively representing the positions of the outer shapes of the solder portions 25*a* and 25*c*.

As exemplified in FIG. 7, the line segments 62*a*, 62*b*, 63*a*, and 63*b* are located on the inner side of the line segments 61*a* and 61*b*. That is, the outer shape of the image sensor 22 includes the outer shape of each of the plurality of wirings 50*a* and 50*c* and that of each of the plurality of solder portions 25*a* and 25*c*.

Similarly, even in a section (not shown) orthogonal to the section 70 shown in FIG. 2, orthogonal to the imaging surface of the image sensor 22, and passing through the wirings 50*b* and 50*d*, the outer shape of the image sensor 22 includes the outer shape of the wiring portion 50*b* and that of the solder portion 25*b*. Furthermore, the outer shape of the image sensor 22 includes the outer shape of the wiring portion 50*d* and a solder portion (not shown) for connecting the wiring portion 50*d* to the extending portion 23*d* of the flexible printed circuit 23.

Therefore, in the first embodiment, the plurality of wirings 50*a* to 50*d* and the plurality of solder portions such as the solder portions 25*a* to 25*c* are located on the inner side of the image sensor 22. Thus, according to the first embodiment, an attempt can be made to downsize the camera head 20. In addition, according to the first embodiment, an attempt can be made to downsize the imaging device 10.

In the first embodiment, when assembling the imaging device 10, the flexible printed circuit 23 is bent so as to be set in a state shown in FIG. 7. That is, each of the plurality of extending portions 23a and 23c is bent so that the outer shape of the image sensor 22 includes the outer shape of each of the plurality of wirings 50a and 50c and that of each of the plurality of solder portions 25a and 25c.

For example, as exemplified in FIG. 7, in the state in which the extending portion 23a is bent, the extending portion 23a includes a bending portion 23a_1 and a flat portion 23a_2. In a sectional view, the bending portion 23a_1 bends with a predetermined radius of curvature. Furthermore, one end of the bending portion 23a_1 is coupled to one end of the connection portion 23e. The flat portion 23a_2 has a flat shape. One end of the flat portion 23a_2 is coupled to the other end of the bending portion 23a_1.

Similarly, in the state in which the extending portion 23c is bent, the extending portion 23c includes a bending portion 23c_1 and a flat portion 23c_2. In a sectional view, the bending portion 23c_1 bends with a predetermined radius of curvature. One end of the bending portion 23c_1 is coupled to the other end of the connection portion 23e. The flat portion 23c_2 has a flat shape. One end of the flat portion 23c_2 is coupled to the other end of the bending portion 23c_1.

In this embodiment, the extending portion 23a is bent so that an angle ϕ1 formed by a direction indicated by an arrow 91 and a direction indicated by an arrow 92 is larger than 0° and smaller than 90° in a sectional view. In this case, as shown in FIGS. 2 and 7, the extending portion 23a extends inward from the connection portion 23e. The direction indicated by the arrow 91 is a direction from a distal end portion 23a_2_1 of the flat portion 23a_2 to a boundary 23a_2_2 between the flat portion 23a_2 and the bending portion 23a_1. The direction indicated by the arrow 92 is a direction from a boundary 23e_c between the connection portion 23e and the bending portion 23c_1 to a boundary 23e_a between the connection portion 23e and the bending portion 23a_1.

Similarly, the extending portion 23c is bent so that an angle ϕ2 formed by a direction indicated by an arrow 93 and a direction indicated by an arrow 94 is larger than 0° and smaller than 90° in a sectional view. In this case, as shown in FIGS. 2 and 7, the extending portion 23c extends inward from the connection portion 23e. The direction indicated by the arrow 93 is a direction from a distal end portion 23c_2_1 of the flat portion 23c_2 to a boundary 23c_2_2 between the flat portion 23c_2 and the bending portion 23c_1. The direction indicated by the arrow 94 is a direction from the boundary 23e_a to the boundary 23e_c.

Note that the extending portions 23b and 23d are bent similar to the above-described extending portions 23a and 23c. That is, the extending portions 23b and 23d are bent so that they extend inward from the connection portion 23e.

As described above, each of the four extending portions 23a to 23d has a so-called tapered shape. Thus, the flexible printed circuit 23 can be bent so that the above-described angles are smaller than 90° without contact between a given extending portion and another extending portion.

Figure 8:
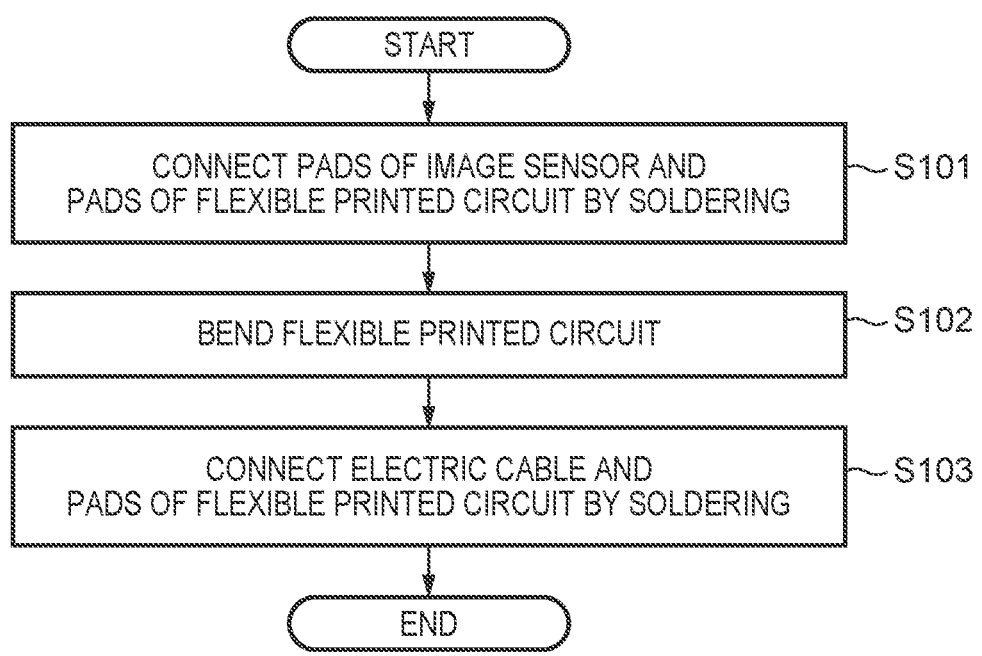
FIG. 8 is a flowchart for explaining an example of a method of connecting the image sensor and the plurality of wirings to the flexible printed circuit according to the first embodiment.

Next, an example of part of a manufacturing method for the imaging device 10 will be described. FIG. 8 is a flowchart for explaining an example of a method of connecting the image sensor 22 and the plurality of wirings 50a to 50d to the flexible printed circuit 23 according to the first embodiment.

The developer who manufactures the imaging device 10 connects the four pads 22a to 22d of the image sensor 22 and the four pads 24a_1 to 24d_1 of the flexible printed circuit 23 by soldering, respectively (step S101).

Then, the developer bends the flexible printed circuit 23 using a jig so that the outer shape of the image sensor 22 includes the outer shape of each of the plurality of wirings 50a to 50d and the outer shape of each of the plurality of solder portions such as the solder portions 25a to 25c (step S102).

Then, the developer connects the four wirings 50a to 50d of the electric cable 50 and the four pads 24a_2 to 24d_2 of the flexible printed circuit 23 by soldering, respectively (step S103).

Note that after steps S101 and S102, the developer may arrange a block (not shown) for pressing the connection portion 23e toward the image sensor 22 in a space surrounded by the plurality of extending portions 23a to 23d of the flexible printed circuit 23. For example, the flexible printed circuit 23 may cause stress deformation by bending in a portion close to the bending portion. For example, a portion close to the bending portion other than the bending portion of the flexible printed circuit 23 may be warped to be separated from the image sensor 22. To cope with this, the block presses the portion toward the image sensor 22 so the portion close to the bending portion of the flexible printed circuit 23 is not warped to be separated from the image sensor 22. This can suppress the portion close to the bending portion of the flexible printed circuit 23 from being warped to be separated from the image sensor 22. This block is an example of a pressing body. If the block is arranged, the camera head 20 includes such block.

The first embodiment has been explained above. Two comparative examples will now be described. The first comparative example will be described.

First Comparative Example

As the first comparative example, a method of connecting a wiring to an image sensor without using a relay board such as a flexible printed circuit will be explained. For example, in an ultra-small imaging device used as an ultra-small endoscope, it is difficult to directly solder a wiring when the image sensor is small. Therefore, it is considered that the distal end of the wiring portion and the pad (terminal portion) of the image sensor are connected by soldering while connecting the wiring portion to the through hole of a ceramic board. This comparative example will be described as the first comparative example.

Figure 9:
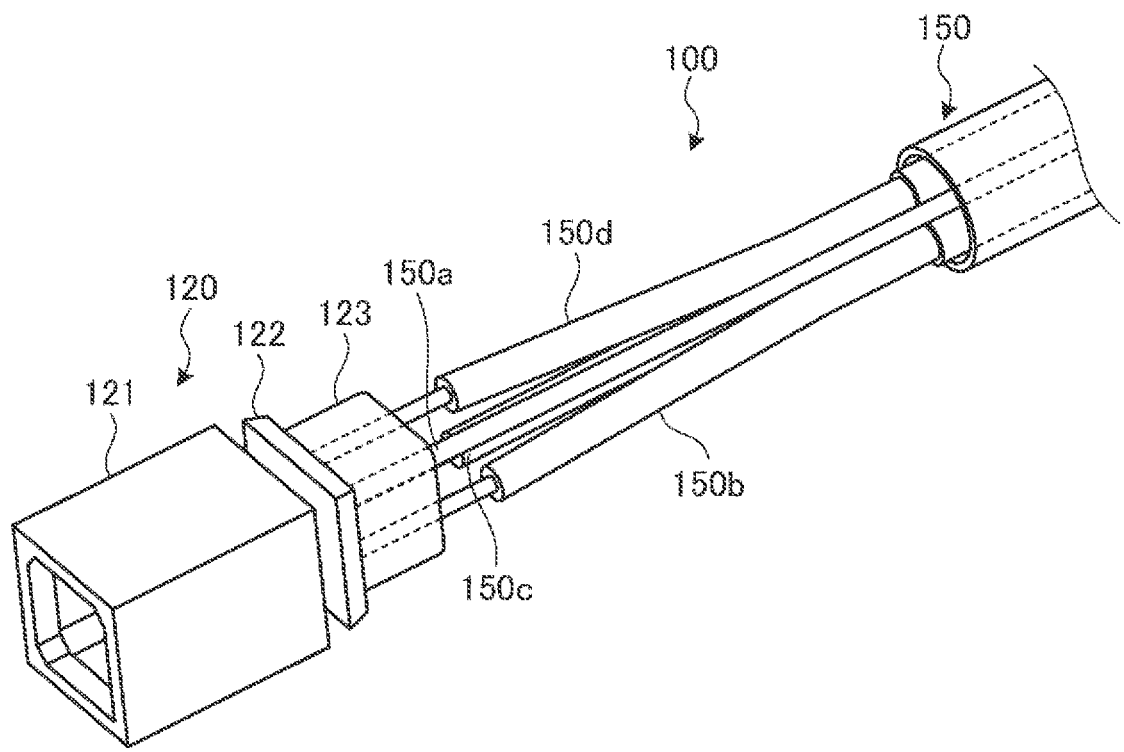
FIG. 9 is a view showing an example of part of the arrangement of an imaging device according to the first comparative example.

FIG. 9 is a view showing an example of part of the arrangement of an imaging device 100 according to the first comparative example. As exemplified in FIG. 9, the imaging device 100 includes, as part of the arrangement, a camera head 120 and an electric cable 150.

The camera head 120 includes a lens housing 121, an image sensor 122, and a ceramic board 123. The image sensor 122 includes four pads (not shown). The electric cable 150 includes four wirings 150a to 150d.

Four through holes are formed in the ceramic board 123. The four wirings 150a to 150d are connected to the four pads of the image sensor 122 via the four through holes, respectively. More specifically, the four wirings 150a to 150d are connected to the four through holes by soldering, respectively, and the distal ends of the four wirings 150a to 150d are connected to the four pads of the image sensor 122 by soldering, respectively.

In the first comparative example, much time is taken to make each wiring portion (150a, 150b, 150c, 150d) pass through each through hole formed in the ceramic board 123. That is, it is difficult to connect each wiring portion (150a, 150b, 150c, 150d) of the electric cable 150 to the ceramic board 123 and the image sensor 122. Furthermore, the size of the ceramic board is very small relative to the diameter of the through hole. Therefore, when a hole for a through hole is formed in the ceramic board, the ceramic board readily breaks. Therefore, in the first comparative example, the yield of the imaging device 100 is low.

On the other hand, in the first embodiment, a work of making a wiring pass through a through hole that takes much time is not performed. In the first embodiment, it is possible to ensure a wide area for each of the plurality of pads $24a\_2$ to $24d\_2$ to which the plurality of wirings 50a to 50d of the electric cable 50 are respectively connected. Therefore, as compared to the first comparative example, in the first embodiment, the developer or the like can readily perform wiring connection to the pads, thereby improving the workability at the time of manufacturing the camera head 20 and the imaging device 10. Furthermore, in the first embodiment, the ceramic board that readily breaks at the time of forming a through hole is not used, unlike the first comparative example. Therefore, in the first embodiment, it is possible to improve the yields of the camera head 20 and the imaging device 10, as compared to the first comparative example.

Second Comparative Example

Figure 10:
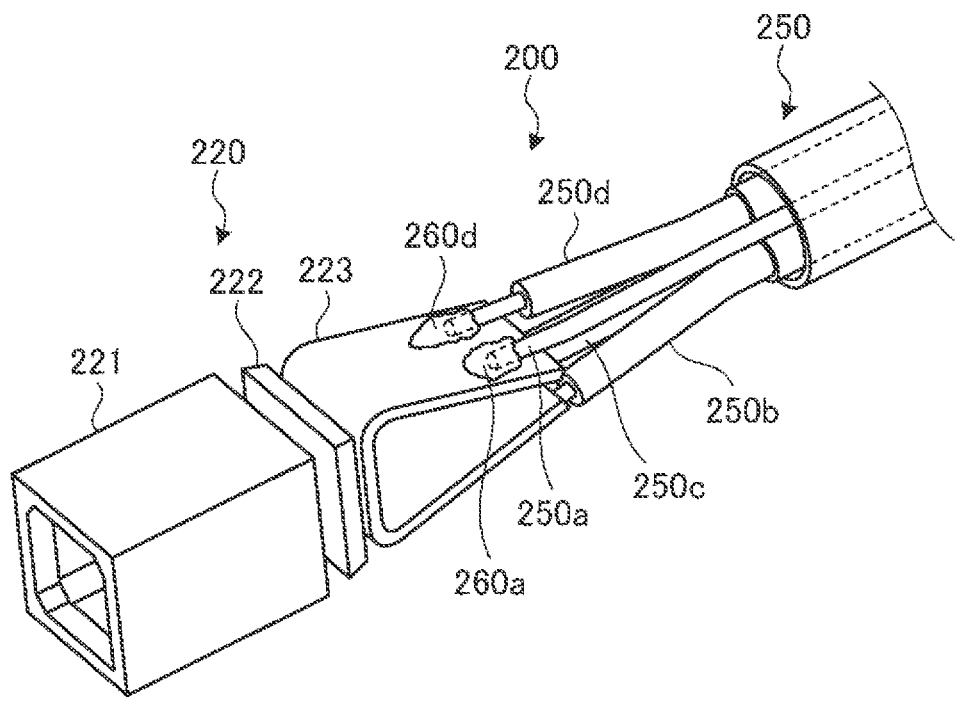
FIG. 10 is a view showing an example of part of the arrangement of an imaging device according to the second comparative example.
Figure 11:
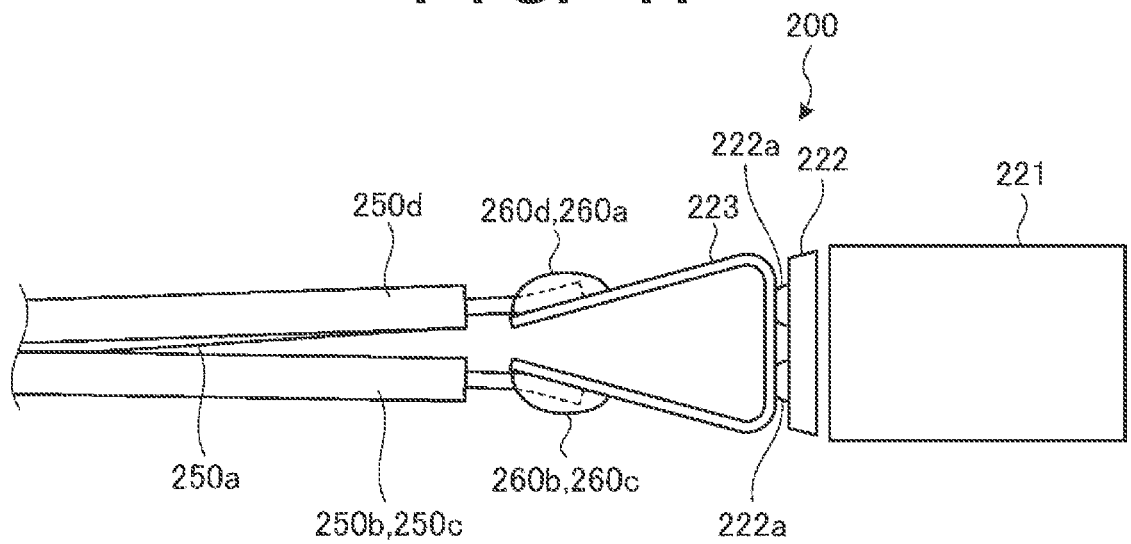
FIG. 11 is a side view of part of the arrangement of the imaging device according to the second comparative example.
Figure 12:
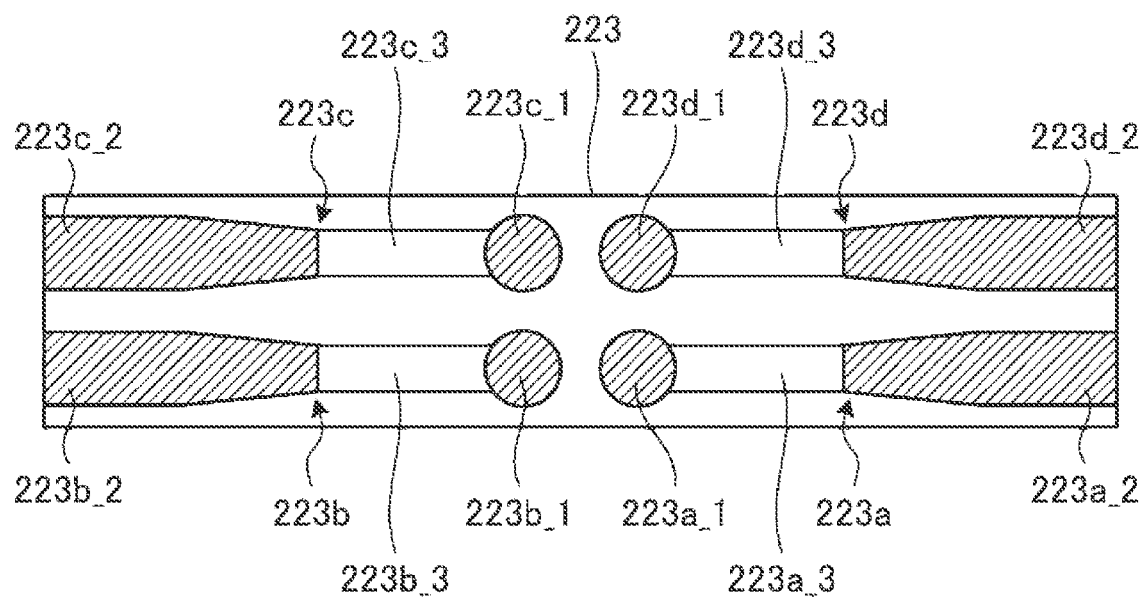
FIG. 12 is a view showing an example of the upper surface of a flexible printed circuit according to the second comparative example.

As the second comparative example, an imaging device in which the distance between a plurality of pads on a flexible printed circuit, which are connected to wirings of an electric cable, is very short will be described. The second comparative example will be described with reference to FIGS. 10 to 12. FIG. 10 is a view showing an example of part of the arrangement of an imaging device 200 according to the second comparative example. FIG. 10 is a perspective view of part of the arrangement of the imaging device 200. FIG. 11 is a side view of part of the arrangement of the imaging device 200 according to the second comparative example. FIG. 12 is a view showing an example of the upper surface of a flexible printed circuit 223 according to the second comparative example. Note that in the second comparative example, the upper surface of the flexible printed circuit 223 indicates a surface on a side connected to an image sensor 222 (to be described later).

As exemplified in FIGS. 10 and 11, the imaging device 200 includes, as part of the arrangement, a camera head 220 and an electric cable 250.

The camera head 220 includes a lens housing 221, the image sensor 222, and the flexible printed circuit 223. The image sensor 222 includes four pads 222a, similar to the image sensor 22 according to the first embodiment. The electric cable 150 includes four wirings 250a to 250d.

As exemplified in FIGS. 10 and 11, in the imaging device 200, the flexible printed circuit 223 is used in a bent state.

Four wirings 223a to 223d are formed on the upper surface of the flexible printed circuit 223. The wiring portion 223a includes a pad $223a\_1$, a pad $223a\_2$, and a wire connection portion $223a\_3$. The wiring portion 223b includes a pad $223b\_1$, a pad $223b\_2$, and a wire connection portion $223b\_3$. The wiring portion 223c includes a pad $223c\_1$, a pad $223c\_2$, and a wire connection portion $223c\_3$. The wiring portion 223d includes a pad $223d\_1$, a pad $223d\_2$, and a wire connection portion $223d\_3$.

The four pads $223a\_1$, $223b\_1$, $223c\_1$, and $223d\_1$ are connected to the four pads 222a via solder portions (not shown) by soldering, respectively.

The four pads $223a\_2$, $223b\_2$, $223c\_2$, and $223d\_2$ are connected to the four wirings 250a to 250d via solder portions by soldering, respectively.

Furthermore, the four wire connection portions $223a\_3$, $223b\_3$, $223c\_3$, and $223d\_3$ electrically connect the four pads $223a\_1$, $223b\_1$, $223c\_1$, and $223d\_1$ and the four pads $223a\_2$, $223b\_2$, $223c\_2$, and $223d\_2$, respectively.

In the second comparative example, as shown in FIG. 12, the two pads $223a\_2$ and $223d\_2$ are adjacent to each other. Thus, it is difficult to ensure a wide area for each of the pads $223a\_2$ and $223d\_2$. For the same reason, it is also difficult to ensure a wide area for each of the pads $223b\_2$ and $223c\_2$. Therefore, in the second comparative example, it is difficult to reliably connect the wirings to the pads.

In the second comparative example, the distance between the adjacent pads $223a\_2$ and $223d\_2$ is short. In addition, the distance between the adjacent pads $223b\_2$ and $223c\_2$ is short. Therefore, a bridge or the like may occur.

On the other hand, according to the first embodiment, as described above, only one pad ($24a\_2$, $24b\_2$, $24c\_2$, $24d\_2$) is provided in one extending portion (23a, 23b, 23c, 23d). Therefore, it is possible to ensure a wide area for a pad. Therefore, in the first embodiment, the developer or the like can readily perform wiring connection to the pads, as compared to the second comparative example.

In the first embodiment, as shown in FIG. 7 above, on the outer surface (upper surface 26) of the flexible printed circuit 23, soldering is performed to connect the wirings such as the wiring portion 50a and the flexible printed circuit 23. The developer or the like can perform soldering on the outer surface more easily than soldering on the inner surface (lower surface 27). Therefore, according to the first embodiment, from this viewpoint as well, the developer or the like can readily perform wiring connection to the pads.

Furthermore, in the first embodiment, in one extending portion, only one pad is provided without arranging a plurality of pads to be adjacent to each other. Thus, according to the first embodiment, it is possible to suppress occurrence of a bridge or the like, as compared to the second comparative example. Therefore, according to the first embodiment, it is possible to readily perform wiring connection while suppressing occurrence of a bridge or the like.

Modification of First Embodiment

Note that the above first embodiment has explained a case in which the flexible printed circuit 23 includes the four extending portions 23a to 23d respectively extending from four portions of the connection portion 23e. However, the flexible printed circuit 23 may include a plurality of extending portions respectively extending from at least three portions of the connection portion 23e. In this case, at least one pad to which at least one of the plurality of wirings of the electric cable 50 is connected is provided in each of the plurality of extending portions. This modification will be described as a modification of the first embodiment.

Figure 13:
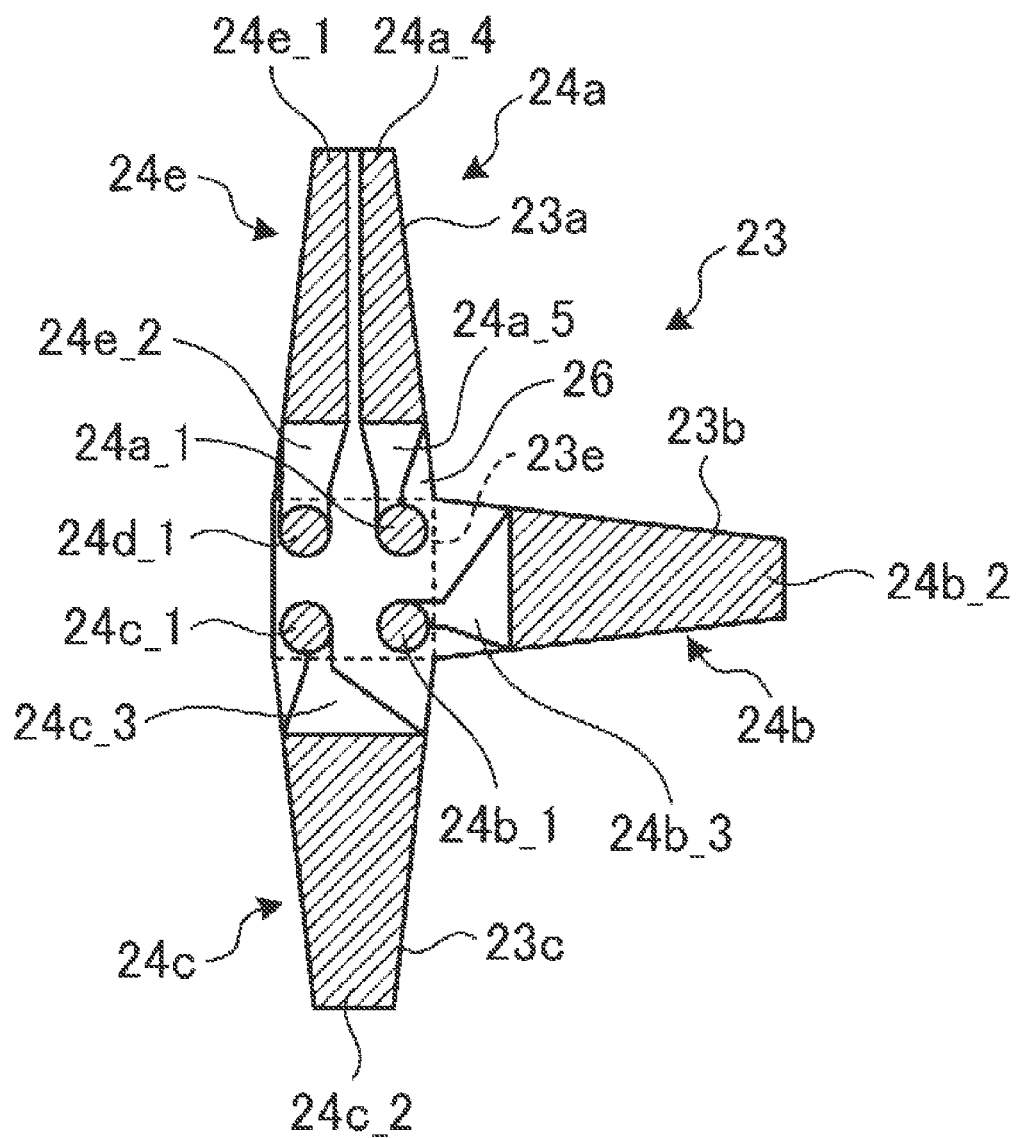
FIG. 13 is a view showing an example of the flexible printed circuit according to a modification of the first embodiment.

Note that the modification of the first embodiment will mainly describe points different from the first embodiment, and a description of the same arrangement and processing as in the first embodiment may be omitted. In addition, in the modification of the first embodiment, the same reference numerals as in the first embodiment denote the same components and a description thereof may be omitted. FIG. 13 is a view showing an example of the flexible printed circuit 23 according to the modification of the first embodiment.

The flexible printed circuit 23 according to the modification is different from the first embodiment in that no extending portion 23d is provided. As exemplified in FIG. 13, the flexible printed circuit 23 includes the plurality (three) of extending portions 23a to 23c respectively extending from three portions of the connection portion 23e. Furthermore, the modification is different from the first embodiment in that the wiring portion 24a includes a pad 24a_4 and a wire connection portion 24a_5 instead of the pad 24a_2 and the wire connection portion 24a_3. The flexible printed circuit 23 according to the modification is different from the first embodiment in that it includes a wiring 24e.

The pad 24a_4 is formed in the extending portion 23a. The pad 24a_4 is connected to the wiring portion 50a, similar to the pad 24a_2 of the first embodiment. However, the area of the pad 24a_4 is smaller than that of the pad 24a_2.

The wire connection portion 24a_5 is formed across the connection portion 23e and the extending portion 23a. The wire connection portion 24a_5 electrically connects the pads 24a_1 and 24a_4. The area of the wire connection portion 24a_5 is smaller than that of the wire connection portion 24a_3 of the first embodiment.

The wiring portion 24e includes the pad 24a_1, a pad 24e_1, and a wire connection portion 24e_2.

The pad 24e_1 is formed in the extending portion 23a. The pad 24e_1 is electrically connected to the wiring portion 50d of the electric cable 50. For example, the pad 24e_1 is connected to the wiring portion 50d via a solder portion (not shown) by soldering. The pad 24e_1 is an example of a wiring pad.

The wire connection portion 24e_2 is formed across the connection portion 23e and the extending portion 23a. The wire connection portion 24e_2 electrically connects the pads 24d_1 and 24e_1. Therefore, the wiring portion 50d and the image sensor 22 are electrically connected to each other.

The modification of the first embodiment has been explained above. In the modification of the first embodiment, only one pad (24b_2, 24c_2) to which one of the plurality of wirings 50a to 50d is connected is provided in each of two extending portions (extending portions 23b and 23c) among the plurality (three) of extending portions 23a to 23c. Thus, it is possible to ensure a wide area for each of the two pads 24b_2 and 24c_2. As described above, in the modification of the first embodiment, a plurality of pads are provided in not all the extending portions, and only one pad is provided in at least one of all the extending portions. Therefore, according to the modification of the first embodiment, the developer or the like can readily perform wiring connection to the pad (for example, the pad 24b_2, 24c_2) to which the wiring portion of the electric cable 50 is connected.

In the modification of the first embodiment, in two of the three extending portions, only one pad is provided without arranging a plurality of pads to be adjacent to each other. As described above, in the modification of the first embodiment, a plurality of pads are provided in not all the extending portions, and only one pad is provided in at least one of all the extending portions. Thus, according to the modification of the first embodiment, it is possible to suppress occurrence of a bridge or the like. Therefore, according to the first embodiment, it is possible to readily perform wiring connection while suppressing occurrence of a bridge or the like.

Note that one pad to which one of the plurality of wirings of the electric cable 50 is connected is provided in at least one of the plurality of extending portions. In this arrangement as well, the developer or the like can readily perform wiring connection to the pad. Furthermore, it is possible to suppress occurrence of a bridge or the like.

Second Embodiment

The above first embodiment has explained a case in which the outer surface (upper surface 26) of the flexible printed circuit 23 in the bent state and the wirings of the electric cable 50 are connected to each other. However, the inner surface of the flexible printed circuit in the bent state and the wirings of the electric cable 50 may be connected to each other. This embodiment will be described as the second embodiment.

In the second embodiment, a through hole is formed as a conductive path passing through a flexible printed circuit. Since such through hole is formed, a pad connected to a wiring of an electric cable 50 can be provided on the inner surface of the flexible printed circuit in a bent state.

Note that the second embodiment will mainly describe points different from the first embodiment, and a description of the same arrangement and processing as in the first embodiment may be omitted. In addition, in the second embodiment, the same reference numerals as in the first embodiment denote the same components and a description thereof may be omitted. FIG. 14 is a view showing an example of the arrangement of a camera head 20a and the electric cable 50 according to the second embodiment.

An imaging device 10 according to the second embodiment is different from the imaging device 10 according to the first embodiment in that it includes the camera head 20a instead of the camera head 20. The camera head 20a according to the second embodiment is different from the camera head 20 according to the first embodiment in that it includes a flexible printed circuit 30 instead of the flexible printed circuit 23. Furthermore, the electric cable 50 according to the second embodiment is different from the electric cable 50 according to the first embodiment in that it includes a wiring 50e instead of the wiring portion 50b.

The wiring portion 50e according to the second embodiment is a wiring through which an image signal is transmitted. The wiring portion 50e includes a core 50e_1 and a covering material 50e_2. The core 50e_1 is a conductor through which the image signal flows. The covering material 50e_2 is made of an insulating material such as vinyl. The covering material 50e_2 covers the core 50e_1. However, as shown in FIG. 14, the distal end portion of the core 50e_1 is not covered with the covering material 50e_2 and is exposed so as to be connectable to an extending portion 30b of the flexible printed circuit 30.

As shown in FIG. 14, the camera head 20a includes a lens housing 21, an image sensor 22, and the flexible printed circuit 30. Although not shown in FIG. 14, the camera head 20a includes solder portions 35a and 35c (see FIG. 17) for electrically connecting wirings 50a and 50c, respectively, to the flexible printed circuit 30. The camera head 20a also includes a solder portion (not shown) for electrically connecting the wiring portion 50e of the electric cable 50 to the flexible printed circuit 30. Furthermore, the camera head 20a includes a solder portion (not shown) for electrically connecting the wiring portion 50d of the electric cable 50 to the flexible printed circuit 30. The camera head 20a is an example of an imaging module.

Figure 15:
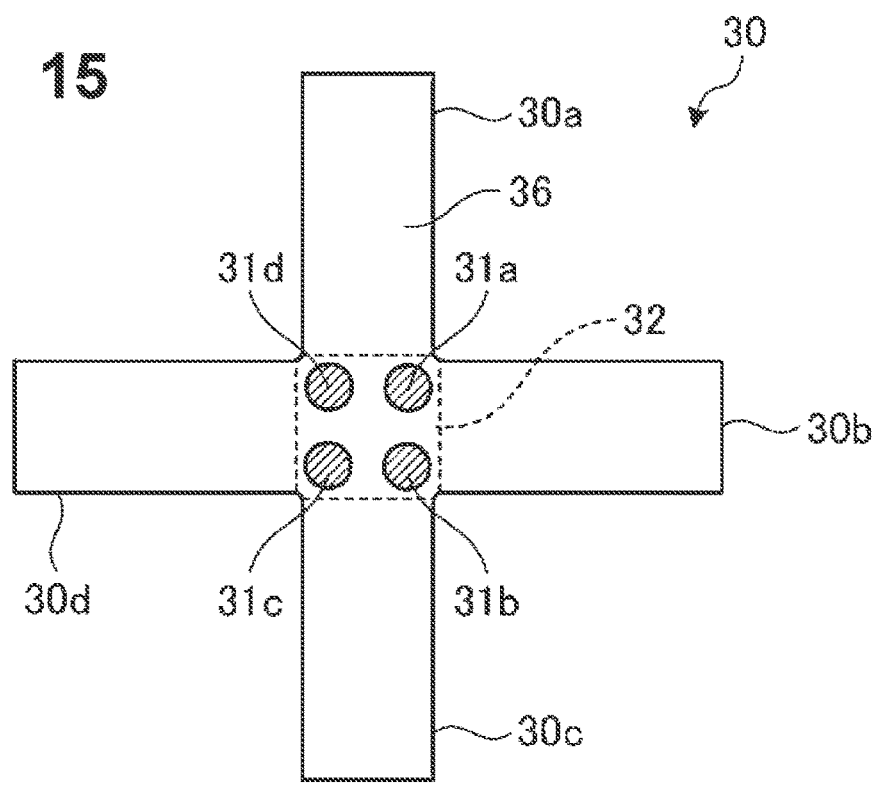
FIG. 15 is a view showing an example of a flexible printed circuit according to the second embodiment.

FIG. 15 is a view showing an example of the flexible printed circuit 30 according to the second embodiment. FIG. 15 is a front view showing an upper surface 36 of the flexible printed circuit 30. Note that in this embodiment, a side of the flexible printed circuit 30 connected to the image sensor 22 is set as an upper side and a surface on the side connected to the image sensor 22 is set as the upper surface 36. The surface on the opposite side of the upper surface 36 of the flexible printed circuit 30 is set as a lower surface 37 (see FIG. 16). The flexible printed circuit 30 is an example of a flexible wiring board. The flexible printed circuit 30 electrically connects the image sensor 22 and the electric cable 50. Note that if the flexible printed circuit 30 is used as a part forming the imaging device 10 according to the second embodiment, the flexible printed circuit 30 is used in the bent state, as shown in FIG. 14. However, FIG. 15 shows an example of the flexible printed circuit 30 in a non-bent state.

The flexible printed circuit 30 is, for example, a double-sided flexible printed circuit (double-sided FPC). As exemplified in FIG. 15, the flexible printed circuit 30 includes a plurality (four) of extending portions 30a to 30d and a connection portion 32. The surface on the upper side of the connection portion 32 is a region (implementation region) where the image sensor 22 is implemented, and is a region (connection region) connected to the image sensor 22. As exemplified in FIG. 15, the four extending portions 30a to 30d extend from the connection portion 32 in four directions. More specifically, the four extending portions 30a to 30d extend in directions different from each other by 90°. The four extending portions 30a to 30d extend from four portions of the connection portion 32 connected to the image sensor 22.

As exemplified in FIG. 15, each of the four extending portions 30a to 30d has a constant width without tapering, unlike the extending portions 23a to 23d according to the first embodiment. That is, each of the four extending portions 30a to 30d has a rectangular shape in a front view.

In the imaging device 10 according to the second embodiment, the flexible printed circuit 30 is bent at the boundary between each of the four extending portions 30a to 30d and the connection portion 23e.

On the upper surface 36 of the flexible printed circuit 30, four pads 31a to 31d are formed. The four pads 31a to 31d are formed in the connection portion 32.

The four pads 31a to 31d are formed at positions corresponding to the pads 22a to 22d of the image sensor 22, respectively. For example, the four pads 31a to 31d are formed at positions facing the pads 22a to 22d, respectively. The four pads 31a to 31d are electrically connected to the pads 22a to 22d, respectively. For example, the four pads 31a to 31d are connected to the pads 22a to 22d via solder portions (not shown) by soldering, respectively.

A through hole (not shown) is formed at a position, in the connection portion 32, corresponding to each of the four pads 31a to 31d. The four pads 31a to 31d are electrically connected to four pads 33b_1, 33c_1, 33d_1, and 33a_1 (to be described later) via the through holes, respectively.

Figure 16:
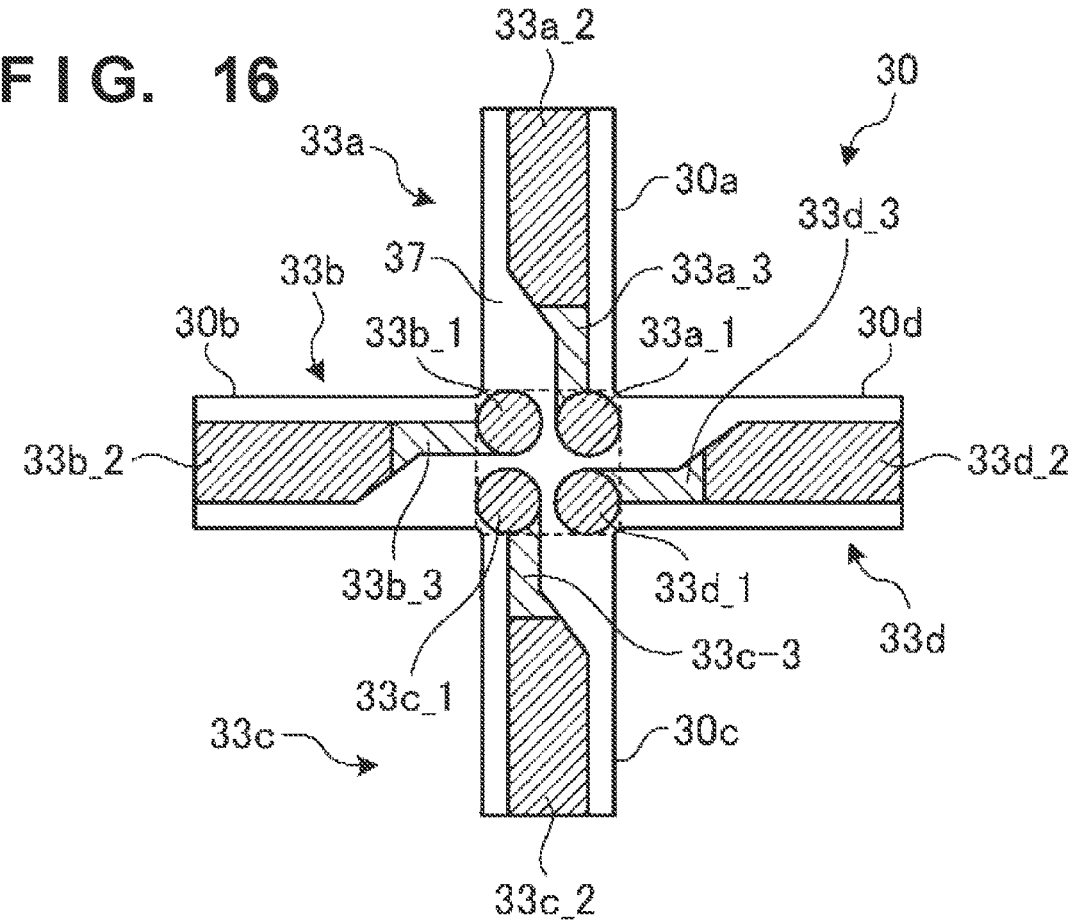
FIG. 16 is a rear view showing the lower surface of the flexible printed circuit.

FIG. 16 is a rear view showing the lower surface 37 of the flexible printed circuit 30. Broken lines shown in FIG. 16 indicate portions where the flexible printed circuit 30 is bent. As exemplified in FIG. 16, four wirings 33a to 33d are formed on the lower surface 37 of the flexible printed circuit 30. The wiring portion 33a includes the pad 33a_1, a pad 33a_2, and a wire connection portion 33a_3.

The pad 33a_1 is formed at a position corresponding to the pad 31d on the side of the upper surface 36. The pad 33a_1 is connected to the pad 31d via the through hole.

The pad 33a_2 is formed in the extending portion 30a. The pad 33a_2 is electrically connected to the wiring portion 50a of the electric cable 50. For example, the pad 33a_2 is connected to the core 50a_1 of the wiring portion 50a via the solder portion 35a (see FIG. 17). The pad 33a_2 is an example of a wiring pad. Note that in the second embodiment, the wiring portion 50a is a power supply wiring portion.

The wire connection portion 33a_3 is formed across the connection portion 32 and the extending portion 30a. The wire connection portion 33a_3 electrically connects the pads 33a_1 and 33a_2. Therefore, the wiring portion 50a and the pad 22d of the image sensor 22 are electrically connected to each other.

The wiring portion 33b includes the pad 33b_1, a pad 33b_2, and a wire connection portion 33b_3.

The pad 33b_1 is formed at a position corresponding to the pad 31a on the side of the upper surface 36. The pad 33b_1 is connected to the pad 31a via the through hole.

The pad 33b_2 is formed in the extending portion 30b. The pad 33b_2 is electrically connected to the wiring portion 50e of the electric cable 50. For example, the pad 33b_2 is connected to the core 50e_1 of the wiring portion 50e via a solder portion (not shown) by soldering. The pad 33b_2 is an example of a wiring pad. Note that in the second embodiment, the wiring portion 50e is a wiring through which the image signal is transmitted.

The wire connection portion 33b_3 is formed across the connection portion 32 and the extending portion 30b. The wire connection portion 33b_3 electrically connects the pads 33b_1 and 33b_2. Therefore, the wiring portion 50e and the pad 22a of the image sensor 22 are electrically connected to each other.

The wiring portion 33c includes the pad 33c_1, a pad 33c_2, and a wire connection portion 33c_3.

The pad 33c_1 is formed at a position corresponding to the pad 31b on the side of the upper surface 36. The pad 33c_1 is connected to the pad 31b via the through hole.

The pad 33c_2 is formed in the extending portion 30c. The pad 33c_2 is electrically connected to the wiring portion 50c of the electric cable 50. For example, the pad 33c_2 is connected to the core 50c_1 of the wiring portion 50c via the solder portion 35c (see FIG. 17) by soldering. The pad 33c_2 is an example of a wiring pad. Note that in the second embodiment, the wiring portion 50c is a wiring used as ground (GND).

The wire connection portion 33c_3 is formed across the connection portion 32 and the extending portion 30c. The wire connection portion 33c_3 electrically connects the pads 33c_1 and 33c_2. Therefore, the wiring portion 50c and the pad 22b of the image sensor 22 are electrically connected to each other.

The wiring portion 33d includes the pad 33d_1, a pad 33d_2, and a wire connection portion 33d_3.

The pad 33d_1 is formed at a position corresponding to the pad 31c on the side of the upper surface 36. The pad 33d_1 is connected to the pad 31c via the through hole.

The pad 33d_2 is formed in the extending portion 30d. The pad 33d_2 is electrically connected to the wiring portion 50d of the electric cable 50. For example, the pad 33d_2 is connected to a core 50d_1 of the wiring portion 50d via a solder portion (not shown) by soldering. The pad 33d_2 is an example of a wiring pad. Note that in the second embodiment, the wiring portion 50d is a wiring through which a synchronization signal is transmitted.

The wire connection portion 33d_3 is formed across the connection portion 32 and the extending portion 30d. The wire connection portion 33d_3 electrically connects the pads 33d_1 and 33d_2. Therefore, the wiring portion 50d and the pad 22c of the image sensor 22 are electrically connected to each other.

As described above, according to this embodiment, only one pad (33a_2, 33b_2, 33c_2, 33d_2) is provided on the inner surface (lower surface 37) of one extending portion (30a, 30b, 30c, 30d). Thus, it is possible to ensure a wide area for one pad. Therefore, according to this embodiment, a developer who performs soldering or the like can readily perform wiring connection to the pad. Furthermore, in one extending portion, only one pad is provided without arranging a plurality of pads to be adjacent to each other. Thus, according to this embodiment, it is possible to suppress occurrence of a bridge or the like. Therefore, according to this embodiment, it is possible to readily perform wiring connection while suppressing occurrence of a bridge or the like.

Furthermore, in this embodiment, as described above, each of the four extending portions 30a to 30d has a constant width without tapering. Therefore, according to this embodiment, it is possible to ensure a wide area for one pad, as compared to the first embodiment.

Next, an example of the positional relationship between the image sensor 22 and each of the plurality of extending portions 30a and 30c of the flexible printed circuit 30 will be described with reference to FIG. 17.

Figure 17:
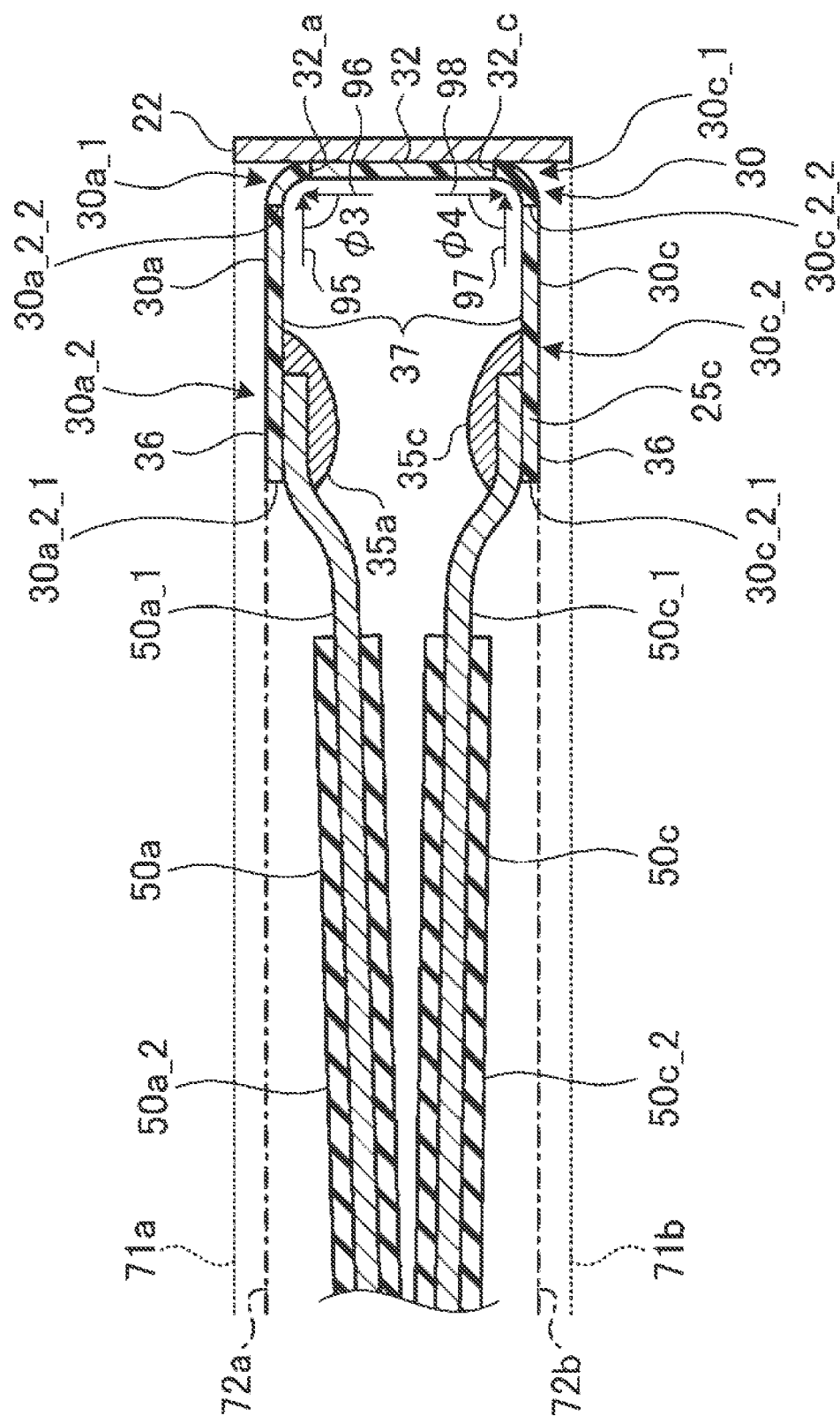
FIG. 17 is a view for explaining an example of the positional relationship between an image sensor and each of a plurality of extending portions.

FIG. 17 is a view for explaining an example of the positional relationship between the image sensor 22 and each of the plurality of extending portions 30a and 30c. FIG. 17 is a sectional view showing a section 71 that is indicated by a broken line in FIG. 14, is orthogonal to the imaging surface of the image sensor 22, and passes through the extending portions 30a and 30c and the wirings 50a and 50c.

FIG. 17 shows, in a sectional view, line segments 71a and 71b representing the position of the outer shape of the image sensor 22 and line segments 72a and 72b respectively representing the positions of the outer shapes of the extending portions 30a and 30c.

As exemplified in FIG. 17, the line segments 72a and 72b are located on the inner side of the line segments 71a and 71b. That is, the outer shape of the image sensor 22 includes the outer shape of the extending portion 30a and that of the extending portion 30c.

Similarly, in this embodiment, even in a section (not shown) orthogonal to the section 71 shown in FIG. 14, orthogonal to the imaging surface of the image sensor 22, and passing through the extending portions 30b and 30d and the wirings 50e and 50d, the outer shape of the image sensor 22 includes the outer shape of the extending portion 30b and that of the extending portion 30d.

Therefore, in the second embodiment, the plurality (four) of extending portions 30a to 30d of the flexible printed circuit 30 are located on the inner side of the image sensor 22. Thus, according to the second embodiment, an attempt can be made to downsize the camera head 20a. In addition, according to the second embodiment, an attempt can be made to downsize the imaging device 10.

In the second embodiment, when assembling the imaging device 10, the flexible printed circuit 30 is bent so as to be set in a state shown in FIG. 17. That is, the extending portions 30a and 30c are bent so that the outer shape of the image sensor 22 includes the outer shape of the extending portion 30a and that of the extending portion 30c.

For example, as exemplified in FIG. 17, in the state in which the extending portion 30a is bent, the extending portion 30a includes a bending portion 30a_1 and a flat portion 30a_2. In a sectional view, the bending portion 30a_1 bends with a predetermined radius of curvature. Furthermore, one end of the bending portion 30a_1 is coupled to one end of the connection portion 32. The flat portion 30a_2 has a flat shape. One end of the flat portion 30a_2 is coupled to the other end of the bending portion 30a_1.

Similarly, in the state in which the extending portion 30c is bent, the extending portion 30c includes a bending portion 30c_1 and a flat portion 30c_2. In a sectional view, the bending portion 30c_1 bends with a predetermined radius of curvature. One end of the bending portion 30c_1 is coupled to the other end of the connection portion 32. The flat portion 30c_2 has a flat shape. One end of the flat portion 30c_2 is coupled to the other end of the bending portion 30c_1.

In this embodiment, the extending portion 30a is bent so that an angle $\phi 3$ formed by a direction indicated by an arrow 95 and a direction indicated by an arrow 96 is almost 90° in a sectional view. In this case, as shown in FIGS. 14 and 17, the extending portion 30a extends from the connection portion 32 in a direction (a direction opposite to the direction indicated by the arrow 95) orthogonal to the imaging surface of the image sensor 22 and away from the image sensor 22. The direction indicated by the arrow 95 is a direction from a distal end portion 30a_2_1 of the flat portion 30a_2 to a boundary 30a_2_2 between the flat portion 30a_2 and the bending portion 30a_1. The direction indicated by the arrow 96 is a direction from a boundary 32_c between the connection portion 32 and the bending portion 30c_1 to a boundary 32_a between the connection portion 32 and the bending portion 30a_1.

Similarly, the extending portion 30c is bent so that an angle $\phi 4$ formed by a direction indicated by an arrow 97 and a direction indicated by an arrow 98 is almost 90° in a sectional view. In this case, the extending portion 30c extends from the connection portion 32 in a direction (a direction opposite to the direction indicated by the arrow 97) orthogonal to the imaging surface of the image sensor 22 and away from the image sensor 22. The direction indicated by the arrow 97 is a direction from a distal end portion 30c_2_1 of the flat portion 30c_2 to a boundary 30c_2_2 between the flat portion 30c_2 and the bending portion 30c_1. The direction indicated by the arrow 98 is a direction from the boundary 32_a to the boundary 32_c.

Note that the extending portions 30b and 30d are bent, similar to the above-described extending portions 30a and 30c. That is, the extending portions 30b and 30d are bent so that they extend from the connection portion 32 in the direction orthogonal to the imaging surface of the image sensor 22 and away from the image sensor 22.

Figure 18:
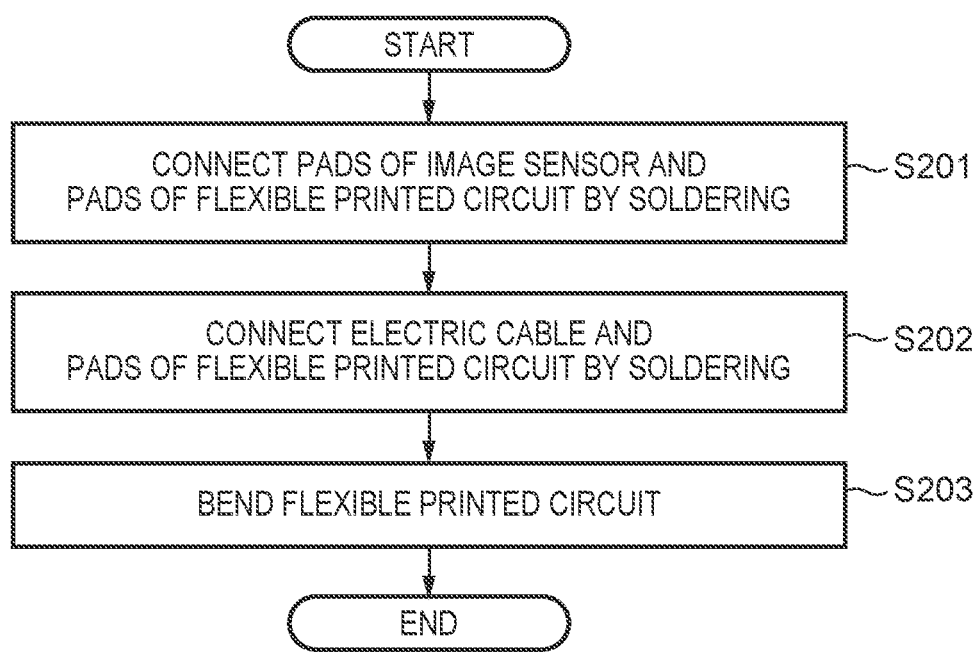
FIG. 18 is a flowchart for explaining an example of a method of connecting the image sensor and a plurality of wirings to the flexible printed circuit according to the second embodiment.

Next, an example of part of a manufacturing method for the imaging device 10 according to the second embodiment will be described. FIG. 18 is a flowchart for explaining an example of a method of connecting the image sensor 22 and the plurality of wirings 50a, 50e, 50c, and 50d to the flexible printed circuit 30 according to the second embodiment.

First, the developer connects the four pads 22a to 22d of the image sensor 22 and the four pads 31a to 31d of the flexible printed circuit 30 by soldering, respectively (step S201).

Then, the developer connects the four wirings 50a, 50e, 50c, and 50d of the electric cable 50 and the four pads 33a_2 to 33d_2 of the flexible printed circuit 30 by soldering, respectively (step S202).

Then, the developer bends the flexible printed circuit 30 using a jig so that the outer shape of the image sensor 22 includes the outer shape of each of the plurality of extending portions 30*a* to 30*d* (step S203).

The second embodiment has been explained above. According to the second embodiment, as described above, the developer or the like can readily perform wiring connection to the pad. Furthermore, according to the second embodiment, as described above, it is possible to suppress occurrence of a bridge or the like. That is, according to the second embodiment, it is possible to readily perform wiring connection while suppressing occurrence of a bridge or the like.

Modification of Second Embodiment

Note that the above second embodiment has explained a case in which the flexible printed circuit 30 includes the four extending portions 30*a* to 30*d* respectively extending from four portions of the connection portion 32. However, the flexible printed circuit 30 may include a plurality of extending portions respectively extending from at least three portions of the connection portion 32. In this case, at least one pad to which at least one of a plurality of wirings of the electric cable 50 is connected is provided in each of the plurality of extending portions. This modification will be described as a modification of the second embodiment.

Figure 19:
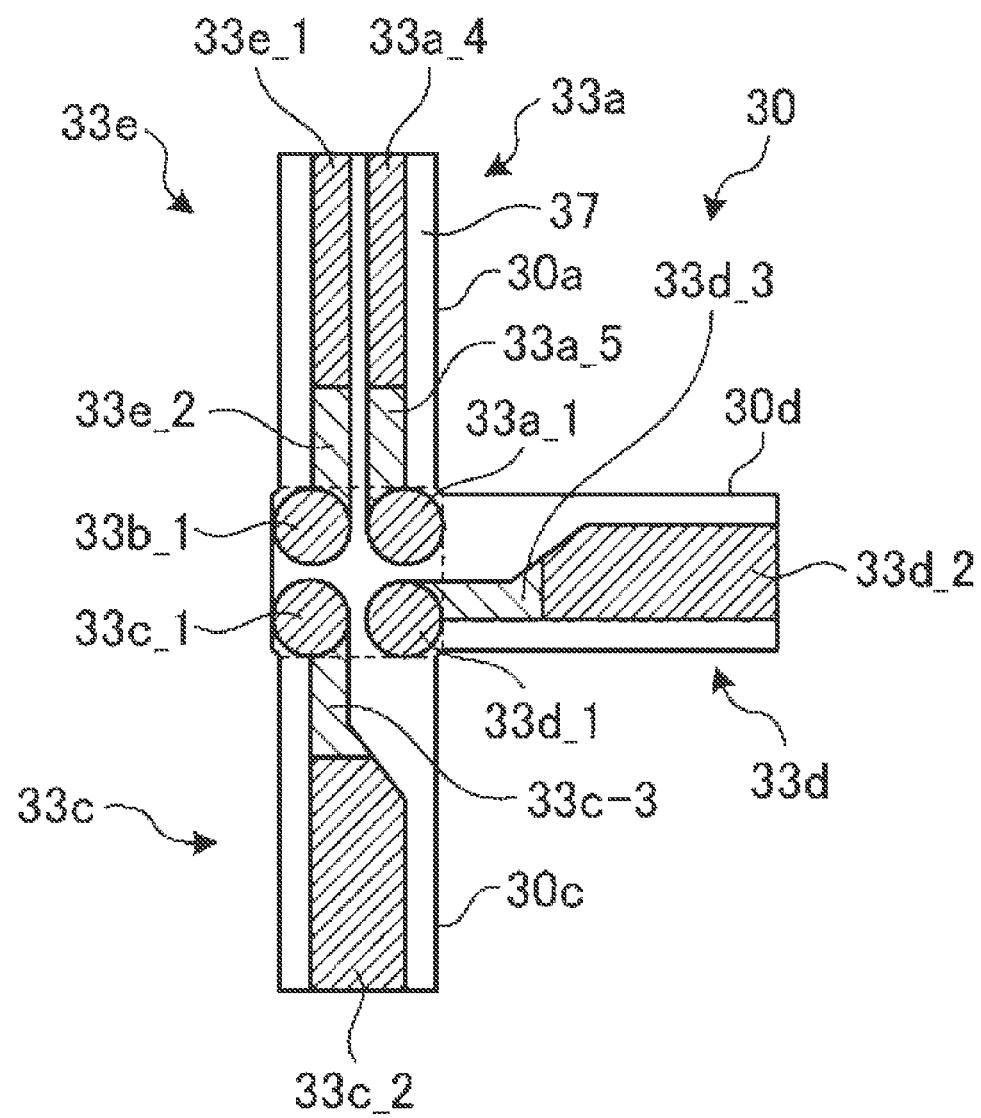
FIG. 19 is a view showing an example of the flexible printed circuit according to a modification of the second embodiment.

Note that the modification of the second embodiment will mainly describe points different from the second embodiment, and a description of the same arrangement and processing as in the second embodiment may be omitted. In addition, in the modification of the second embodiment, the same reference numerals as in the second embodiment denote the same components and a description thereof may be omitted. FIG. 19 is a view showing an example of the flexible printed circuit 30 according to the modification of the second embodiment.

The flexible printed circuit 30 according to the modification is different from the second embodiment in that no extending portion 30*b* is provided. As exemplified in FIG. 19, the flexible printed circuit 30 includes the plurality (three) of extending portions 30*a*, 30*c*, and 30*d* respectively extending from three portions of the connection portion 32 (see FIG. 15). Furthermore, the modification is different from the second embodiment in that the wiring portion 33*a* includes a pad 33*a*_4 and a wire connection portion 33*a*_5 instead of the pad 33*a*_2 and the wire connection portion 33*a*_3. The flexible printed circuit 30 according to the modification is different from the second embodiment in that it includes a wiring 33*e*.

The pad 33*a*_4 is formed in the extending portion 30*a*. The pad 33*a*_4 is connected to the wiring portion 50*a*, similar to the pad 33*a*_2 of the second embodiment. However, the area of the pad 33*a*_4 is smaller than that of the pad 33*a*_2.

The wire connection portion 33*a*_5 is formed across the connection portion 32 and the extending portion 30*a*. The wire connection portion 33*a*_5 electrically connects the pads 33*a*_1 and 33*a*_4. The area of the wire connection portion 33*a*_5 is smaller than that of the wire connection portion 33*a*_3 of the second embodiment.

The wiring portion 33*e* includes the pad 33*b*_1, a pad 33*e*_1, and a wire connection portion 33*e*_2.

The pad 33*e*_1 is formed in the extending portion 30*a*. The pad 33*e*_1 is electrically connected to the wiring portion 50*e* of the electric cable 50. For example, the pad 33*e*_1 is connected to the core 50*e*_1 of the wiring portion 50*e* via a solder portion (not shown) by soldering. The pad 33*e*_1 is an example of a wiring pad.

The wire connection portion 33*e*_2 is formed across the connection portion 32 and the extending portion 30*a*. The wire connection portion 33*e*_2 electrically connects the pads 33*b*_1 and 33*e*_1. Therefore, the wiring portion 50*e* and the pad 22*a* of the image sensor 22 are electrically connected to each other.

The modification of the second embodiment has been explained above. In the modification of the second embodiment, only one pad (33*c*_2, 33*d*_2) to which one of the plurality of wirings 50*a*, 50*e*, 50*c*, and 50*d* is connected is provided in each of two extending portions (extending portions 30*c* and 30*d*) among the plurality (three) of extending portions 30*a*, 30*c*, and 30*d*. Thus, it is possible to ensure a wide area for each of the two pads 33*c*_2 and 33*d*_2. As described above, in the modification of the second embodiment, a plurality of pads are provided in not all the extending portions, and only one pad is provided in at least one of all the extending portions. Therefore, according to the modification of the second embodiment, the developer or the like can readily perform wiring connection to the pad (for example, the pad 33*c*_2, 33*d*_2) to which the wiring portion of the electric cable 50 is connected.

In the modification of the second embodiment, in two of the three extending portions, only one pad is provided without arranging a plurality of pads to be adjacent to each other. As described above, in the modification of the second embodiment, a plurality of pads are provided in not all the extending portions, and only one pad is provided in at least one of all the extending portions. Thus, according to the modification of the second embodiment, it is possible to suppress occurrence of a bridge or the like. That is, according to the modification of the second embodiment, it is possible to readily perform wiring connection while suppressing occurrence of a bridge or the like.

Note that each of the above embodiments and modifications has explained a case in which the imaging device 10 is used as an ultra-small medical endoscope. For example, the camera head 20 or 20*a* is provided in a scope having a diameter of about 1 mm. That is, each of the above embodiments and modifications has explained a case in which the extremely small image sensor 22 is connected by thin long wirings under a condition that the directions and positions of the wirings are restricted. However, the imaging device 10 may be used for a device other than an ultra-small medical endoscope. For example, under the condition that the above restriction is imposed, the imaging device 10 may be used for an ultra-small industrial endoscope that needs to connect an image sensor by wirings.

According to at least one of the above-described embodiments and modifications, it is possible to readily perform wiring connection while suppressing occurrence of a bridge or the like.

Although several embodiments of the present invention have been explained, these embodiments are presented as examples, and are not intended to limit the scope of the invention. These embodiments can be practiced in a variety of other forms, and various omissions, replacements, and changes can be made without departing from the spirit and scope of the invention. These embodiments and their modifications are incorporated in the spirit and scope of the invention, and are also incorporated within the range of inventions and their equivalents described in the scope of claims.

REFERENCE SIGNS LIST

10 imaging device
20, 20*a* camera head 22 image sensor
23, 30 flexible printed circuit
50 electric cable

The invention claimed is:
1. An imaging module comprising:
an electric cable including a plurality of wirings;
an imager having an imaging surface intersecting an axial direction of a distal end of the electric cable; and
a flexible wiring board configured to electrically connect the imager and the electric cable, the wiring board including a plurality of extending portions that extend from at least three portions of a connection portion that is connected to the imager, and
at least one wiring pad to which at least one of the plurality of wirings of the electric cable is connected is provided in each of the plurality of extending portions,
wherein each of the plurality of extending portions has a width that decreases as a distance from the connection portion increases and extends inward from the connection portion.
2. The imaging module according to claim 1, wherein one wiring pad to which one of the plurality of wirings is connected is provided in at least one of the plurality of extending portions.
3. The imaging module according to claim 1, wherein one wiring pad to which each of the plurality of wirings is connected is provided in each of the plurality of extending portions.
4. The imaging module according to claim 3, wherein the electric cable includes four wirings as the plurality of wirings, and the wiring board includes four extending portions as the plurality of extending portions, and
wherein one wiring pad to which each of the four wirings is connected is provided in each of the four extending portions.
5. The imaging module according to claim 1, wherein each of the plurality of extending portions extends in a direction perpendicular to the imaging surface, and
wherein the wiring pad is provided on an inner surface of each of the plurality of extending portions.
6. The imaging module according to claim 1, further comprising a pressing body configured to press the connection portion toward the imager.
7. An imaging device comprising an imaging module defined in claim 1.
8. The imaging module according to claim 1, wherein in a state that the plurality of extending portions are bent, an outer shape of the flexible wiring board is included within an outer shape of the imager.
9. An imaging module comprising:
an electric cable including four wirings;
an imager having an imaging surface intersecting an axial direction of a distal end of the electric cable; and
a flexible wiring board configured to electrically connect the imager and the electric cable, the wiring board including four extending portions that extend from a connection portion that is connected to the imager,
wherein a wiring pad to which a corresponding one of the four wirings is connected is provided in each of the four extending portions, each of the four extending portions having a width that decreases as a distance from the connection portion increases, and each of the four extending portions is bent with respect to the connection portion so as to approach the axial direction of the electric cable as the distance from the connection portion increases, and
wherein, in a state that the four extending portions are bent, an outer shape of the flexible wiring board is included within an outer shape of the imager.
10. The imaging module according to claim 9, wherein each of the four extending portions extends in a direction perpendicular to the imaging surface, and
wherein the wiring pad is provided on an inner surface of each of the four extending portions.
11. The imaging module according to claim 9, further comprising a pressing body configured to press the connection portion toward the imager.
12. The imaging module according to claim 9, wherein the connection portion has a shape of a rectangular, and each of the four extending portions extends from a corresponding side of the four sides of the rectangular.
13. An imaging device comprising an imaging module defined in claim 9.

* * * * *